United States Patent
Allen-Vercoe et al.

(10) Patent No.: US 10,314,864 B2
(45) Date of Patent: Jun. 11, 2019

(54) MEDIA SUPPLEMENTS AND METHODS TO CULTURE HUMAN GASTROINTESTINAL ANAEROBIC MICROORGANISMS

(71) Applicant: University of Guelph, Guelph (CA)

(72) Inventors: Emma Allen-Vercoe, Guelph (CA); Julie McDonald, Guelph (CA)

(73) Assignee: Nubiyota LLC, Teaneck, NJ (US)

( * ) Notice: Subject to any disclaimer, the term of this patent is extended or adjusted under 35 U.S.C. 154(b) by 0 days.

(21) Appl. No.: 15/440,906

(22) Filed: Feb. 23, 2017

(65) Prior Publication Data
US 2017/0319633 A1     Nov. 9, 2017

Related U.S. Application Data

(63) Continuation of application No. 14/344,967, filed as application No. PCT/CA2012/050641 on Sep. 14, 2012, now abandoned.

(60) Provisional application No. 61/534,456, filed on Sep. 14, 2011.

(51) Int. Cl.
| | | |
|---|---|---|
| A61K 35/74 | (2015.01) | |
| C12N 1/20 | (2006.01) | |
| C12R 1/145 | (2006.01) | |
| C12R 1/01 | (2006.01) | |
| A61K 35/745 | (2015.01) | |
| A61K 35/747 | (2015.01) | |

(52) U.S. Cl.
CPC ............ *A61K 35/74* (2013.01); *A61K 35/745* (2013.01); *A61K 35/747* (2013.01); *C12N 1/20* (2013.01); *C12R 1/01* (2013.01); *C12R 1/145* (2013.01)

(58) Field of Classification Search
None
See application file for complete search history.

(56) References Cited

PUBLICATIONS

Tannock Eur. J.Clinical Nutrition (2002) 56, Supplement 4: S44-S49 (Year: 2002).*

* cited by examiner

*Primary Examiner* — Susan M Hanley
(74) *Attorney, Agent, or Firm* — Greenberg Traurig, LLP

(57) ABSTRACT

A media supplement for culturing anaerobic bacteria is provided which comprises a filtrate of eilluent from a chemostat vessel in which a target bacterial ecosystem has been culnn-ed. Methods of using the supplement for culturing or isolating anaerobic microbial strains or communities, particularly anaerobic bacteria from the human gut, are also provided.

7 Claims, 28 Drawing Sheets

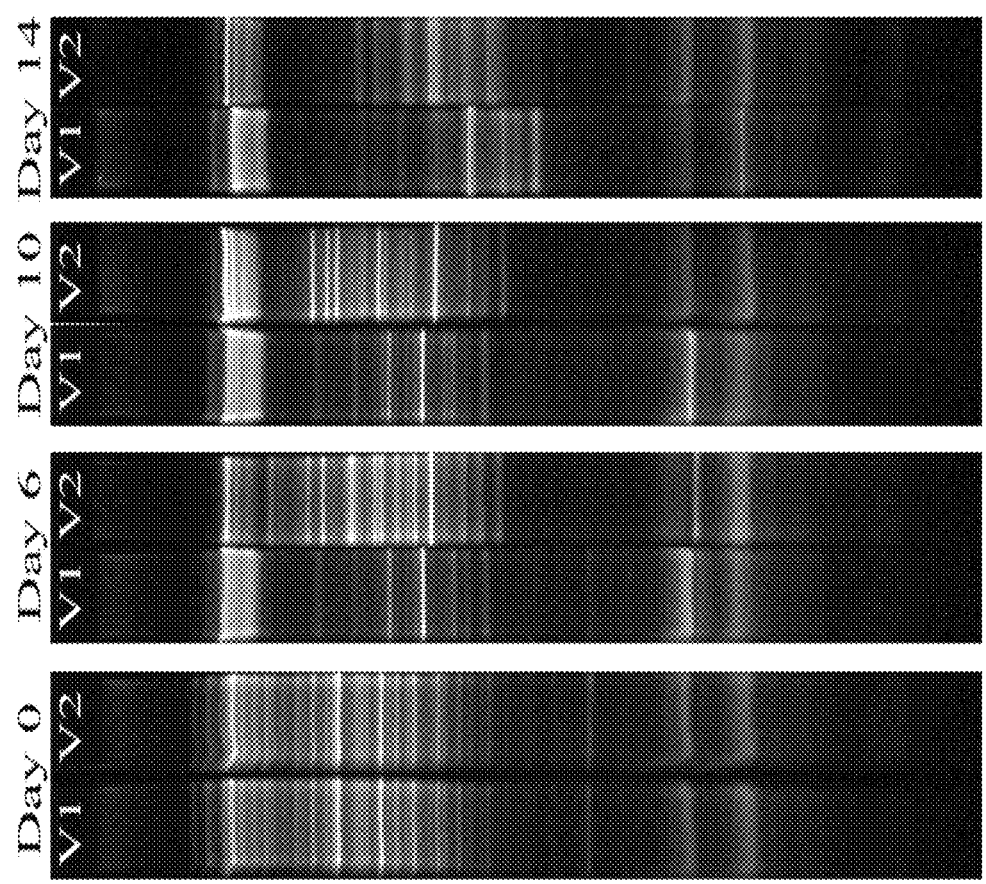

MEDIA SUPPLEMENTS AND METHODS TO CULTURE HUMAN GASTROINTESTINAL ANAEROBIC MICROORGANISMS

RELATED APPLICATIONS

This application is a continuation of U.S. application Ser. No. 14/344,967, filed on May 5, 2014, which is a 371 national phase application off of international application no. PCT/CA2012/050641, filed Sep. 14, 2012, which claims priority to U.S. provisional application No. 61/534,456, filed on Sep. 14, 2011, the entire contents of which are hereby incorporated by reference.

FIELD OF THE INVENTION

This invention relates to methods for culturing microbial communities from the human distal colon and methods for isolating anaerobic microbes from such communities, as well as media supplements for use in such methods.

BACKGROUND OF THE INVENTION

The human gut is the most densely inhabited ecosystem on Earth (Marchesi and Shanahan, 2007). Like other complex microbial ecosystems, the human microbiota has not been sampled to completion (Eckburg et al., 2005). This is because the individual species of the gut microbiota are difficult to culture axenically in vitro (Hart et al., 2002). In fact, of the 500+ bacterial species which colonize the human intestinal tract, about 75% have not been cultured using conventional techniques (Duncan et al., 2007; Eckburg et al., 2005; Hayashi et al., 2002). It is recognized that novel culture techniques are required to grow these "unculturable" microorganisms.

Studies of gut microbiota have been hampered by a lack of model systems. While in vivo models can provide researchers with physiologically relevant experimental models, they have several drawbacks. For example, different study participants can each have unique, host-specific community profiles representing their gut microbiota, making comparison of the gut microbiota between subjects difficult, especially when attempting to correlate the effects of a treatment to changes in the gut microbiota. In vivo models also often limit the dynamic monitoring of the gut microbiota by deriving their data from end-point measurements. Experiments involving humans or animals require research ethics approval which can limit the experiments conducted on an individual's gut microbiota in vivo.

In an attempt to improve upon the drawbacks of in vivo models, several in vitro models have been developed. These in vitro systems range from simple batch culture vessels to complex continuous culture or 'chemostat' systems (Macfarlane, G. T. and Macfarlane, S., Curr. Opin. Biotechnol., 18(2): 156-62, 2007). Using chemostats, communities seeded from fresh feces can reach a steady-state that closely resembles in vivo distal gut communities. Being a host-free system, chemostats supporting gut microbiota make ideal vessels in which to study microbial perturbations that directly result from the addition of exogenous stimuli in isolation from the effects of these stimuli on host physiology, making them useful for mechanistic studies (Macfarlane, G. T. and Macfarlane, S., Curr. Opin. Biotechnol., 18(2): 156-62, 2007).

In vitro models also provide several other advantages over in vivo models in studies of the human gut microbiota. In vitro studies are generally inexpensive and easy to set-up. They also allow for the strict control of factors that influence the environment while still facilitating frequent and simple sampling of the simulated gut communities. However, while chemostats provide a useful tool to investigate the microbial ecology of the gut, operational parameters vary widely between different models in different laboratories, often without experimental validation. Preparation of the inocula, composition of the media, and retention time of the vessel are parameters which can vary between different studies.

To represent a valid model of the human distal gut, communities which develop within chemostat vessels should share some similarity to the fecal inoculum from which the gut community was derived. The microbial ecosystem of the gut is a highly diverse community, and it is therefore important that communities grown in artificial systems also retain a high level of diversity (including species richness and evenness). Finally, the reproducibility and stability of these communities must be established and characterized before experimentation can begin. This means that microbial communities developed within these models must be thoroughly analyzed and compared to in vivo communities before the validity of a system can be confirmed.

Chemostat and fecal communities can be monitored using molecular methods such as Denaturing Gradient Gel Electrophoresis (DGGE). Currently, there is a lack of standardization between DGGE analysis methods used in different research laboratories. Methods of DGGE analysis vary from visual inspection to methods utilizing statistical analysis software (such as GelCompar™, BioNumerics, GeneTools, Quantity One™, etc.). Monitoring of communities using computer software allows for more reliable and detailed analysis of DGGE gels and provides more data on the composition and structure of microbial communities, the stability of the community, and the similarity between profiles. However, laboratories utilizing these analysis programs do not use consistent methods when analyzing their DGGE gels and report varying data on their communities. If the analysis of DGGE gels can be standardized then this will facilitate the comparison between the chemostat communities from different laboratories.

It would be desirable therefore to be provided with chemostat models of the human distal gut that are stable, reproducible and biologically significant, as well as more complete methods for the assessment and verification of such models.

SUMMARY OF THE INVENTION

There are provided herein methods for culturing microorganisms that normally live in the human large intestine. Methods for developing and characterizing microbial communities from the human distal colon and for assessing and/or verifying such communities are provided herein.

In an aspect, there are provided methods for culturing microorganisms from the human distal colon using a media supplement termed "Liquid Gold". Liquid Gold refers to a 0.2 μm filtrate of spent culture media or effluent from a chemostat vessel in which a target ecosystem is cultured. Liquid Gold is used to supplement culture media, e.g., standard laboratory media. Supplementation with Liquid Gold allows culturing of "unculturable" microorganisms, i.e., microorganisms which are refractory to culture axenically using traditional methods. Without wishing to be limited by theory, it is believed that Liquid Gold provides 'growth signals' to previously uncultured microbes to enhance their axenic growth in vitro and hence allow them to be cultured and grown in vitro. It is known in the art that certain microbes may grow well within a microbial ecosystem, but are refractory to growth in isolation; presumably the larger bacterial community in the ecosystem in some way "supports" the growth of the microbes. We report herein that this support can be provided by Liquid Gold to allow isolation of certain microbes and to establish their growth as a pure isolate in vitro, separate from the rest of the ecosystem.

Thus, in an aspect there is provided a method for growing anaerobic bacteria comprising culturing the bacteria in a chemostat under conditions replicating normal human colonic gastrointestinal tract in equilibrium and then purifying individual anaerobic bacteria into pure isolates.

In another aspect, there are provided microbial communities from the human distal colon. In an embodiment, there is provided a single-stage chemostat model of the human distal gut. In an embodiment, microbial communities are stable, reproducible, and/or biologically significant.

In another aspect, there is provided herein a media supplement for culturing microbes termed "Liquid Gold." "Liquid Gold" refers to filtered effluent from the chemostat, i.e., the effluent forced out of the chemostat through pressure differentials; it drips into sterile bottles, housed behind the chemostat, via tubing. When the bottle is full, it is sealed and can be stored at +4° C. until needed. The effluent is passed through a 0.2 µm, e.g, a 0.22 µm filter (Durapore, Millipore, USA), to remove bacterial cells to produce cell-free Liquid Gold, which is used to supplement culture media (usually added to 1% v/v, 3% v/v, 5% v/v, 7% v/v or 10% v/v). Liquid Gold is essentially supernatant from a culture of microbes, containing a plethora of signaling molecules, growth factors and so on. In an embodiment, Liquid Gold is used to supplement culture media at 3% v/v. It should be understood that Liquid Gold will differ depending on the microbial community from which it is produced.

In an embodiment, there is provided a media supplement for culturing anaerobic bacteria, the media supplement comprising a filtrate of effluent from a chemostat vessel in which a target bacterial ecosystem has been cultured. The filtrate may be, e.g., a 0.2 µm filtrate. In one embodiment, the culture media in which the target bacterial ecosystem is cultured is standard culture media. In another embodiment, the culture media is Media 1. In an embodiment, the culture media comprises mucin. Mucin may be present in the culture media at a concentration of about 1-10%. In an embodiment, mucin is present in the culture media at a concentration of 4 g/L. In an embodiment, a human fecal sample has been cultured in the chemostat. The human fecal sample may be, for example, a 10% w/v fecal slurry supernatant or a 20% w/v fecal slurry supernatant. In another embodiment, Defined Experimental Community 1 (DEC-1), Defined Experimental Community 2 (DEC-2) or Defined Experimental Community 3 (DEC-3) has been cultured in the chemostat. In yet another embodiment, the target bacterial ecosystem comprises at least one, at least three, at least five, at least 8, at least 10, at least 15, or at least 25 of the bacterial strains listed in Table 1, Table 2 or Table 3. In a further embodiment, the target ecosystem which has been cultured in the chemostat comprises a community of bacterial strains representing an enterotype of human gut, e.g., the *Bacteroides*, the *Prevotella* or the *Ruminococcus* enterotype. In another embodiment, the anaerobic bacteria are bacteria found in the human gut microbiome.

In an embodiment, the chemostat vessel used in the methods and preparations of the invention is a single-stage chemostat.

In an embodiment, there is provided a media supplement for culturing anaerobic bacteria, wherein the media supplement is prepared by: a) culturing a target bacterial ecosystem in culture media in a single-stage chemostat under conditions replicating normal human colonic gastrointestinal tract, in equilibrium; b) collecting effluent from the chemostat; and c) filtering the effluent through a 0.2 µm filter to remove bacterial cells, in order to produce the media supplement. In an embodiment, the method for preparing the media supplement further comprises a step of centrifuging the effluent at 14,000 rpm for 10 minutes and collecting the supernatant before step c), wherein the effluent supernatant is then filtered in step c). In another embodiment, the method for preparing the media supplement further comprises filtering the effluent or effluent supernatant sequentially through a 1.0 µm filter, a 0.8 µm filter, and a 0.45 µm filter, before filtering through the 0.2 µm filter. In an embodiment, the 0.2 µm filter is a 0.22 µm filter. The culture media may be, e.g., standard culture media or Media 1.

In an embodiment, the target bacterial ecosystem is obtained by culturing a human fecal sample, e.g., a 10% w/v fecal slurry supernatant or a 20% w/v fecal slurry supernatant. In another embodiment, the target bacterial ecosystem comprises Defined Experimental Community 1 (DEC-1), Defined Experimental Community 2 (DEC-2), or Defined Experimental Community 3 (DEC-3). In another embodiment, the target bacterial ecosystem comprises a community of bacterial strains representing an enterotype of human gut, e.g., the *Bacteroides*, the *Prevotella* or the *Ruminococcus* enterotype. In yet another embodiment, the target bacterial ecosystem comprises at least one, at least three, at least five, at least 8, at least 10, at least 15, or at least 25 of the bacterial strains listed in Table 1, Table 2 or Table 3.

In an embodiment, the culture media is Media 1. In another embodiment, the culture media comprises mucin, e.g., at a concentration of 1-10%, e.g., at a concentration of 4 g/L. In an embodiment, the chemostat is a single-stage chemostat. In an embodiment, the chemostat has a system retention time of 24 hours. In another embodiment, the conditions replicating normal human colonic gastrointestinal tract comprise: a temperature of about 37° C.; a pH of about 6.9 to 7; a system retention time of 24 hours; and maintenance of anaerobic conditions in the chemostat. In another embodiment, the conditions replicating normal human colonic gastrointestinal tract further comprise culturing the target bacterial ecosystem in culture media containing mucin, e.g., mucin at a concentration of 1-10%, e.g., 4 g/L.

In an embodiment, there is provided herein a use of the media supplement of the invention for growing anaerobic bacteria, wherein the media supplement is used to supplement culture media in a liquid culture at about 1% v/v to about 10% v/v. In an embodiment, the media supplement is used to supplement culture media at about 3% v/v. In an embodiment, the liquid culture is grown in a chemostat. The media supplement may be added to the culture media before culturing begins, or during culturing of the anaerobic bacteria. There is also provided herein a use of the media supplement of the invention for growing anaerobic bacteria, wherein the media supplement is used to supplement solid culture media, e.g., solid culture media in a Petri dish. In an embodiment, the media supplement is added to FAA plates at a final concentration of 3%.

In some embodiments, for the uses provided herein, the anaerobic bacteria are bacteria found in human gut of a healthy subject. In an embodiment, the anaerobic bacteria are *Faecalibacterium prausnitzii* or *Ruminococcus callidus* (ATCC27760).

In an embodiment, there is provided herein a method of isolating anaerobic bacteria from human gut, comprising: a) culturing a target bacterial ecosystem in culture media (e.g., standard culture media, Media 1) in a single-stage chemostat under conditions replicating normal human colonic gastrointestinal tract, until equilibrium is reached; b) diluting the culture and plating onto Fastidious anaerobe agar (FAA) supplemented with the media supplement of the invention, and optionally supplemented with defibrinated sheep blood; c) incubating plates in an anaerobe chamber; d) purifying individual anaerobic bacterial colonies grown in step (c); and e) optionally, culturing the purified individual anaerobic bacterial colonies from step (d) in liquid culture in a single-stage chemostat under conditions replicating normal human colonic gastrointestinal tract, optionally wherein the media supplement of the invention is used to supplement culture media at about 1% v/v to about 10% v/v; such that isolates of anaerobic bacteria are obtained. In an embodiment, the media supplement is used to supplement the culture media in step (e) at about 3% v/v. In another embodiment, the media supplement is added at a final concentration of 3% in step (b). In yet another embodiment, the defibrinated sheep blood is added at a final concentration of 5%. In a still further embodiment, the conditions replicating normal human colonic gastrointestinal tract comprise: a temperature of about 37° C.; a pH of about 6.9 to 7; a system retention time of 24 hours; and maintenance of anaerobic conditions in the chemostat. In an embodiment, the conditions replication normal human colonic gastrointestinal tract further comprise culturing in culture media to which mucin has been added. In an embodiment, bacteria are cultured in the chemostat in steps (a) and (e) under reduced atmosphere with controlled levels of partial pressure of $N_2:CO_2:H_2$. For example, the preparation may be under $N_2$, $CO_2$ or $H_2$, or a mixture thereof. In an embodiment, the mixture thereof is $N_2:CO_2:H_2$. In another embodiment, anaerobic conditions are maintained by bubbling filtered nitrogen gas through the cultures in steps (a) and (e).

In some embodiments, the target bacterial ecosystem cultured in step (a) is a human fecal sample, e.g., a 10% w/v fecal slurry supernatant or a 20% w/v fecal slurry supernatant. In an embodiment, standard culture media is used in the chemostat. In an embodiment, Media 1 is used in the chemostat.

In an embodiment, *Faecalibacterium prausnitzii* or *Ruminococcus callidus* (ATCC27760) is isolated. In another embodiment, a pure isolate of *Faecalibacterium prausnitzii*, *Clostridium aldenense* 1, *Clostridium aldenense* 2, *Clostridium hathewayi* 1, *Clostridium hathewayi* 2, *Clostridium hathewayi* 3, *Clostridium thermocellum*, *Ruminococcus bromii* 2, *Ruminococcus torques* 4, *Ruminococcus torques* 5, *Clostridium cocleatum* (e.g., *Clostridium cocleatum* 21 FAA1), *Eubacterium desmolans* (e.g., *Eubacterium desmolans* 48FAA1), *Eubacterium limosum* 13LG, *Lachnospira pectinoshiza*, *Ruminococcus productus* (e.g., *Ruminococcus productus* 27FM), *Ruminococcus obeum* (e.g., *Ruminococcus obeum* 11FM1), *Blautia producta*, or *Clostridium thermocellum* is obtained.

In an embodiment, there is provided herein a pure isolate of *Faecalibacterium prausnitzii*, *Clostridium aldenense* 1, *Clostridium aldenense* 2, *Clostridium hathewayi* 1, *Clostridium hathewayi* 2, *Clostridium hathewayi* 3, *Clostridium thermocellum*, *Ruminococcus bromii* 2, *Ruminococcus torques* 4, *Ruminococcus torques* 5, *Clostridium cocleatum* (e.g., *Clostridium cocleatum* 21 FAA1), *Eubacterium desmolans* (e.g., *Eubacterium desmolans* 48FAA1), *Eubacterium limosum* 13LG, *Lachnospira pedinoshiza*, *Ruminococcus productus* (e.g., *Ruminococcus productus* 27FM), *Ruminococcus obeum* (e.g., *Ruminococcus obeum* 11FM1), *Blautia producta*, or *Clostridium thermocellum*. A pure isolate may be obtained, e.g., using methods provided herein.

In an embodiment, there is provided a method of culturing a microbial community from human gut, comprising: a) obtaining a fecal sample from a healthy human subject; b) inoculating a culture with the fecal sample; and c) culturing the culture in culture media (e.g., standard culture media, Media 1, etc.) in a single-stage chemostat under conditions replicating normal human colonic gastrointestinal tract, until equilibrium is reached; such that a microbial community comprising bacterial strains found in human gut is obtained. In an embodiment, the microbial community represents a human gut enterotype. In another embodiment, the fecal sample obtained in step (a) is prepared as a 10% w/v fecal slurry supernatant or a 20% w/v fecal slurry supernatant before inoculating the culture in step (b).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to preferred embodiments of the present invention, and in which:

FIGS. 7A-F show a comparison of a 65 hour retention time (V1) to a 24 hour retention time (V2). The same fecal inoculum (from Donor 2, 10%) was used to seed each vessel. A) DGGE profiles showing communities on days 0, 6, 10 and 14; B) Correlation coefficients (expressed as percentages) comparing the profiles of each vessel at the same time point, plotted over the course of the experiment; C) Community dynamics as shown using moving window correlation analysis. Similarity of the community within each vessel was calculated by comparing the profile of day (x) and day (x−2); D) Shannon Diversity Index (H') plot representing the community diversity of each vessel over the course of the experiment; E) Range weighted richness (Rr) plot representing the richness in each vessel over the course of the experiment; F) Shannon equitability index ($E_H$) plot representing the community evenness values from each vessel over the course of the experiment. Increasing the retention time from the biologically significant value of 24 hours to 65 hours resulted in a community which was less similar to its inoculum and did not maintain a higher level of diversity.

DETAILED DESCRIPTION OF THE INVENTION

Figure 1:
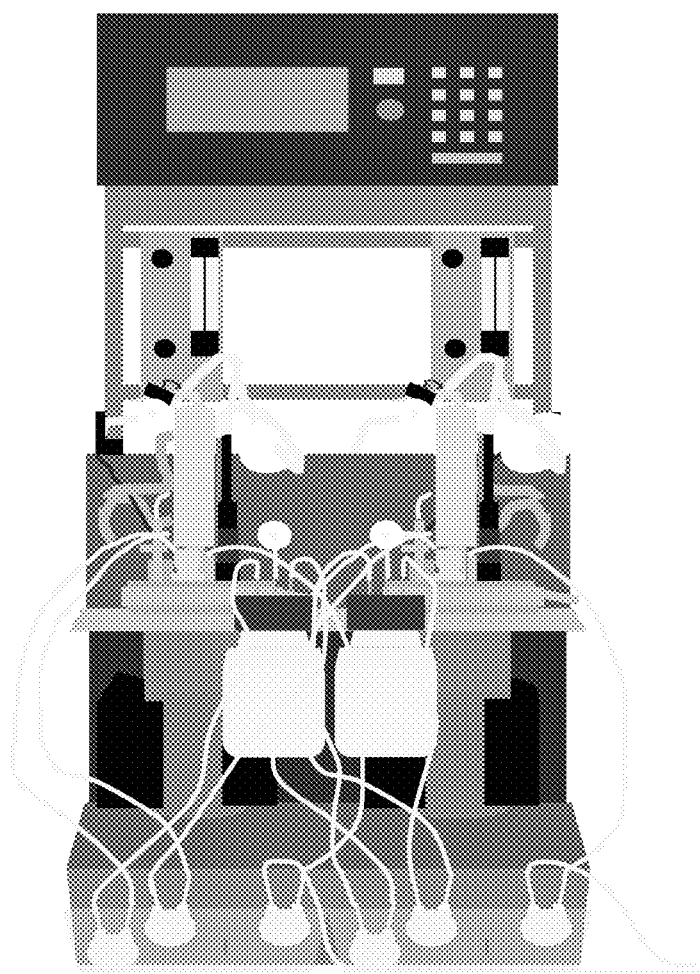
FIG. 1 shows a single-stage chemostat vessel developed by modifying a Multifors fermentation system which was used for growing the isolated bacterial strains as described herein.

According to a broad aspect of the invention there are provided herein novel methods of culturing anaerobic microorganisms or microbes using a single-stage chemostat system. There is also provided a novel media supplement, termed "Liquid Gold," for use in culturing such microorganisms or microbes, in particular those which are traditionally difficult to grow. Methods provided herein can be used, inter alia, to culture enterotypes of the human gut and to provide models of bacterial communities of the human distal colon. Methods provided herein are particularly suited to culturing anerobic bacteria, such as those found in the human gut.

The human gastrointestinal tract contains vast numbers of bacteria, collectively called the intestinal microbiota. The commensal gut flora contribute to host defense by priming the dendritic cells of the immune system, producing bactericidal products that kill pathogenic bacteria, inhibiting the colonization of pathogenic bacteria and competing with pathogens for food and for binding sites along the intestinal epithelial cell surface, a phenomenon collectively known as "colonization resistance" (Stecher B. and Hardt W. D., Trends Microbiol. (2008), 16:107-14; Rolfe, R. D., Infect. Immun. (1984), 45:185-91).

Recent studies have suggested that intestinal or gut enterotypes may not be specific to an individual but, rather, are representative of different states of equilibrium that exist in the gut microbiota in response to dietary stimuli. It has been reported that the human gut microbiome, that is, the community of organisms that live symbiotically within humans, occurs in certain set varieties or "enterotypes. "Three main enterotypes of the human gut, which vary in species and functional composition, have been identified to date, and are termed *Bacteroides, Prevotella* and *Ruminococcus* (Arumugam, M. et al., Nature 12; 473(7346): 174-80, Epub Apr. 20, 2011).

In an aspect, there are provided herein culture methods for culturing enterotypes of the human gut. As reported herein, we harvested fecal samples from donors of each enterotype and used a single-stage chemostat system to culture a bacterial community modelling the community of the donor's distal intestine or gut. Thus, in an embodiment there are provided herein methods for culturing bacterial communities which model enterotypes of the human gut. Methods provided herein can be used to form microbial communities which are stable, reproducible, diverse, and/or biologically significant, in terms of modeling the human distal colon. As reported herein, steady-state communities are generally produces at about one-month, e.g., at approximately 26 days, post-inoculation with a fecal sample, using methods described herein.

In addition, there are provided herein three Defined Experimental Communities (DECs) of microorganisms from human fecal samples. As described, using methods provided herein we subcultured fecal samples from donors representing different enterotypes. Fecal samples were harvested and used to generate DECs of microorganisms modeling enterotypes of the human gut. In an embodiment, three DECs (referred to herein as DEC-1, DEC-2 and DEC-3) are provided.

DEC-1 comprises intestinal bacterial strains that were isolated and purified from donor stool from a donor who had not received antibiotics in the last 5 years (this donor is also referred to herein as "Donor 6"). DEC-1 includes 33-strains (representing a total of 26 species), as shown in Table 1; this DEC has been used successfully to treat two patients (Kingston General Hospital) with recurrent Closiridioides (*Clostridium*) *difficile* infection, demonstrating that the DEC successfully models a microbial community of the human distal colon. Strains were speciated using the 16S rRNA full-length sequence and the GreenGenes database accessible via Lawrence Berkeley National Laboratory (lbl) website.

DEC-2 (from the same donor as DEC-1) includes all the strains in DEC-1 as well as additional bacterial species. Bacterial strains included in DEC-2 are shown in Table 3.

DEC-3 includes isolates of bacterial species shown in Table 2. DEC-3 was isolated from a male donor, 43 yrs old, with no history of antibiotic use in the 6 years prior to stool donation (referred to herein as "Donor 5"). Notably, DEC-3 contains a number of microbes which are either known or speculated to be highly beneficial and enriched in healthy individuals, such as *Akkermansia muciniphila, Faecalibacterium prausnitzii, Bifidobacterium* spp., and *Adlercreutzia equolifasciens.*

In an embodiment, methods are provided herein for culturing bacterial communities which model enterotypes of the human gut use a single-stage chemostat system. This system has been optimized for growing gastrointestinal microbes. In an embodiment, there is provided a chemostat system using the following culture media, referred to herein as "Media 1": Peptone (0.4% w/v); Yeast extract (0.4% w/v); NaHCO3 (0.4% w/v); Pectin (from citrus, 0.4% w/v); Xylan (from beechwood, 0.4% w/v); Arabinogalactan (0.4% w/v); Casein (0.6% w/v); unmodified wheat starch (1% w/v); inulin (0.2% w/v); bile salts (0.1% w/v); L-cysteine HCl (0.1% w/v); CaCl2 (0.0002% w/v); NaCl (0.0002% w/v); K2HPO4 (0.0008% w/v); KH2PO4 (0.0008% w/v); MgSO4 (0.0002% w/v); Hemin (0.0001% w/v); menadione (0.00002% w/v); mucin (porcine, 0.004% w/v)

In an embodiment, the culture media used in methods of the invention, e.g., standard culture media, Media 1, etc., further comprises mucin. It will be understood by the skilled artisan that mucin from any source which is available and affordable can be used. For example, mucin from mammalian sources, such as bovine mucin, porcine mucin, etc., may be used. In an embodiment, porcine mucin is used.

In another embodiment, there is provided herein a media supplement termed "Liquid Gold" and its use to supplement standard laboratory culture media to enhance growth capabilities for microbes that were otherwise considered "unculturable," such as, e.g., certain gastrointestinal, anaerobic microbes. "Liquid Gold" refers to the effluent from a chemostat in which a bacterial community is grown, i.e., the effluent forced out of the chemostat through pressure differentials. Effluent drips into sterile bottles, housed behind the chemostat, via tubing. When the bottle is full, it can be sealed and stored at +4° C. until needed. The effluent is passed through a filter, e.g., a 0.22 µm filter, to remove bacterial cells to produce cell-free Liquid Gold, which is used to supplement culture media.

The optimal amount of Liquid Gold to be added to a culture will vary depending on experimental conditions and the microbes to be grown, and will be determined by the skilled artisan using standard techniques. In an embodiment, Liquid Gold is added to 1% v/v, 3% v/v, 5% v/v, 7% v/v or 10% v/v. In a particular embodiment, Liquid Gold is used to supplement growth media at 3% v/v.

Liquid Gold is essentially a supernatant from a microbial culture and includes a plethora of signaling molecules, growth factors, and so on. It should be understood that the composition of a Liquid Gold preparation will depend on the microbial community from which it is produced. Different types of Liquid Gold can thus be made by growing different bacterial communities in a chemostat. For example, "Native Liquid Gold" is produced from chemostat effluent from culturing complete native feces in a chemostat, e.g., a single-stage chemostat system, as described below. "DEC Liquid Gold" is produced from chemostat effluent from culturing a Defined Experimental Community (such as, e.g., DEC-1) in a chemostat, e.g., a single-stage chemostat system, as described below. As used herein, "DEC-1 Liquid Gold" refers to Liquid Gold produced from chemostat effluent from culturing the DEC-1 community; "DEC-2 Liquid Gold" refers to Liquid Gold produced from chemostat effluent from culturing the DEC-2 community; and "DEC-3 Liquid Gold" refers to Liquid Gold produced from chemostat effluent from culturing the DEC-3 community. As reported herein, fecal samples were harvested from donors of different enterotypes and cultured, and we were therefore able to produce several different types of Liquid Gold media supplement, including, e.g., DEC-1 Liquid Gold, DEC-2 Liquid Gold, DEC-3 Liquid Gold, and Native Liquid Gold.

TABLE 1

Intestinal bacterial strains isolated and purified from donor stool in DEC-1.

| Closest species match, inferred by alignment of 16SrRNA sequence to GreenGenes database* | % identity to closest match | Relative abundance (by biomass) in DEC-1 |
|---|---|---|
| *Acidaminococcus intestinalis* | 100 | +++ |
| *Bacteroides ovatus* | 99.52 | + |
| *Bifidobacterium adolescentis* | 99.79 | ++ |
| (2 different strains) | 99.79 | ++ |
| *Bifidobacterium longum* | 99.86 | +++ |
| (2 different strains) | 99.16 | +++ |
| *Blautia producta*** | 96.43 | + |
| *Clostridium cocleatum* | 91.92 | + |
| *Collinsella aerofaciens* | 98.73 | + |
| *Dorea longicatena* | 99.62 | + |
| (2 different strains) | 99.60 | + |
| *Escherichia coli* | 99.80 | + |
| *Eubacterium desmolans* | 94.90 | + |
| *Eubacterium eligens* | 98.15 | +++++ |
| *Eubacterium limosum* | 97.05 | + |
| *Eubacterium rectale* | 99.59 | +++++ |
| (4 different strains) | 99.60 | +++++ |
| | 99.19 | +++++ |
| | 99.53 | +++++ |
| *Eubacterium ventriosum* | 100 | ++ |
| *Faecalibacterium prausnitzii* | 99.17 | +++++ |
| *Lachnospira pectinoshiza* | 95.22 | + |
| *Lactobacillus casei/paracasei* | 99.47 | + |
| *Lactobacillus casei* | 99.74 | + |
| *Parabacteroides distasonis* | 99.45 | ++ |
| *Raoultella* sp. | 99.40 | + |
| *Roseburia faecalis* | 99.65 | ++ |
| *Roseburia intestinalis* | 100 | ++ |
| *Ruminococcus torques* | 99.15 | +++ |
| (2 different strains) | 99.29 | +++ |
| *Ruminococcus obeum* | 94.89 | + |
| (2 different strains) | 94.69 | + |
| *Streptococcus mitis*$^\Psi$ | 99.79 | + |

*Closest species match was inferred by alignment of 16SrRNA sequence to GreenGenes database; note that in some cases 16S rRNA gene sequences could not resolve identity beyond genus, and that closest match does not infer definitive speciation. Shaded boxes indicate strains that are likely novel species (and in some cases, genera).

Note
that some representative strains identify with the same species by 16S rRNA gene sequence alignment, but we believe them to be different strains based on differences in colony morphology, antibiotic resistance patterns and growth rates.
**Also referred to as *Ruminococcus productus.*
$^\Psi$Identifies with Strep. mitis but is not α-hemolytic.

TABLE 2

Intestinal bacterial strains isolated and purified from donor stool in DEC-3.

| No. | Strain | Closest species$^c$ | % ID$^a$ |
|---|---|---|---|
| 1 | 11 TSAB | *Adlercreutzia equolifaciens* | 99.76% |
| 2 | 18 FAA SS | *Akkermansia muciniphila* | 100% |
| 3 | 9 FAA NB | *Alistipes finegoldii* | 99.27% |
| 4 | 19 D5 FAA | *Alistipes putredinis* | 97.15% |
| 5 | 15 D5 FAA | *Alistipes shahii* | 99.85% |
| 6 | 5 D5 FAA SS | *Alistipes* sp. | 100% |
| 7 | 5 D5 FAA | *Bacteroides capillosus* | 96.98% |
| 8 | 12 FAA | *Bacteroides cellulosilyticus* | 99.46% |
| 9 | 9 D5 FAA | *Bacteroides eggerthii* | 100% |
| 10 | 1 D6 FAA SS | *Bacteroides ovatus* | 100% |
| 11 | 23 FAA | *Bacteroides thetaiotaomicron* | 100% |
| 12 | 1 TSAB | *Bacteroides uniformis* | 100% |
| 13 | 17 BHI | *Bacteroides vulgatus* | 99.85% |
| 14 | 3 FAA SS AER. | *Bacillus circulans* | 100% |

TABLE 2-continued

Intestinal bacterial strains isolated and purified from donor stool in DEC-3.

| No. | Strain | Closest species[c] | % ID[a] |
|---|---|---|---|
| 15 | 1 D5 FAA SS AER. | Bacillus simplex | 98.70% |
| 16 | 1 D6 FAA | Bifidobacterium longum | 100% |
| 17 | 18 D6 FAA SS | Blautia hydrogenotrophica | 100% |
| 18 | 8 FAA | Blautia sp. | 99.15% |
| 19 | 4 TSA SS | Blautia/Clostridium coccoides | 99.85% |
| 20 | 1 D6 FAA SS AER. | Brevibacillus parabrevis | 97.60% |
| 21 | 3 MRS SS | Catabacter hongkongensis | 98.65% |
| 22 | 16 TSA SS | Catabacter sp. | 99.05% |
| 23 | 10 TSAB | Catenibacterium mitsuokai | 99.40% |
| 24 | 13 D6 FAA SS | Clostridium aldenense 1 | 92.04% |
| 25 | 21 D6 FAA SS | Clostridium aldenense 2 | 92.24% |
| 26 | 13 D5 FAA SS | Clostridium asparagiforme | 94.37% |
| 27 | 3 D6 FAA SS | Clostridium bolteae | 99.84% |
| 28 | 6 D5 FAA | Clostridium celerecrescens | 94.48% |
| 29 | 13 D6 FAA | Clostridium hathewayi 1 | 92.19% |
| 30 | 21 FAA NB SS | Clostridium hathewayi 2 | 91.28% |
| 31 | 10 FAA | Clostridium hathewayi 3 | 92.99% |
| 32 | 11 FAA | Clostridium hathewayi 4 | 98.64% |
| 33 | 6 D6 FAA SS | Clostridium hylemonae 1 | 99.85% |
| 34 | 8 D5 FAA SS | Clostridium hylemonae 2 | 97.85% |
| 35 | 5 FAA SS | Clostridium inocuum | 99.12% |
| 36 | 11B D5 FAA SS | Clostridium lavalense | 99.08% |
| 37 | 16 D5 FAA SS | Clostridium leptum | 93.92% |
| 38 | 4 TSA | Clostridium orbiscindens | 96.21% |
| 39 | 14 TSA | Clostridium ramosum | 96.14% |
| 40 | 5 D6 FAA SS | Clostridium scindens | 99.82% |
| 41 | 16 BHI SS | Clostridium staminisolvens | 95.40% |
| 42 | 17 D5 FAA SS | Clostridium sulfatireducens | 96.63% |
| 43 | 2 FAA SS | Clostridium symbiosum | 99.83% |
| 44 | 16 BHI | Clostridium thermocellum | 90.83% |
| 45 | 18 D5 FAA | Clostridium sp. 1 | 99.16% |
| 46 | 2 BHI SS | Clostridium sp. 2 | 97.16% |
| 47 | 20 D5 FAA | Clostridium sp. 3 | 95.51% |
| 48 | 16 D6 FAA SS | Clostridium sp. 4 | 98% |
| 49 | 9 D5 FAA SS | Clostridium sp. 5 | 97.88% |
| 50 | 5 TSA | Clostridium sp. 6 | 96.95% |
| 51 | 6 FAA | Collinsella aerofaciens | 100% |
| 52 | 17 D5 FAA | Coprococcus catus | 99.19% |
| 53 | 1 BHI | Coprococcus comes | 99.70% |
| 54 | 13 FAA | Coprococcus eutactus | 96.49% |
| 55 | 5 NA | Dorea formicigenerans | 99.49% |
| 56 | 1 D5 FAA | Dorea longicatena | 100% |
| 57 | 1 FAA SS AER. | Escherichia coli | 100% |
| 58 | 5 TSAB | Eubacterium biforme | 98.76% |
| 59 | 11 NA SS | Eubacterium callanderi | 98.08% |
| 60 | 19 FAA NB SS | Eubacterium dolichum | 93.23% |
| 61 | 20 FAA | Eubacterium eligens | 96.78% |
| 62 | 9 TSAB SS | Eubacterium fissicatena | 97.67% |
| 63 | 1 BHI SS | Eubacterium limosum | 99.25% |
| 64 | 5 D6 FAA | Eubacterium rectale | 100% |
| 65 | 13 BHI | Eubacterium siraeum | 93.57% |
| 66 | 8 MRS | Eubacterium ventriosum | 97.37% |
| 67 | 22 D6 FAA | Eubacterium xylanophilum 1 | 97.39% |
| 68 | 15 FAA SS | Eubacterium xylanophilum 2 | 96.53% |
| 69 | 23 D6 FAA SS | Eubacterium sp. | 94.31% |
| 70 | 5 FAA NB | Faecalibacterium prausnitzii[b] | 100% |
| 71 | 24 FAA | Gemmiger/Subdoligranulum formicilis/variabile 1 | 98.79% |
| 72 | 19 D5 FAA SS | Gemmiger/Subdoligranulum formicilis/variabile 2 | 95.18% |
| 73 | 17 D6 FAA SS | Holdemania filiformis | 97.51% |
| 74 | 1 FAA NB SS AER. | Microbacterium schlefferi | 99.34% |
| 75 | 7 FAA NB SS AER. | Micrococcus luteus | 97.04% |
| 76 | 21 D6 FAA | Odoribacter splanchnicus | 100% |
| 77 | 24 D6 FAA SS | Oscillibacter valericigenes | 95.16% |
| 78 | 6 FAA NB | Oscillibacter sp. | 98.74% |
| 79 | 16 FAA | Parabacteroides gordonii | 99.81% |
| 80 | 6 D6 FAA | Parabacteroides merdae | 100% |
| 81 | 10 D5 FAA SS | Parasutterella excrementihominis | 100% |
| 82 | 22 FAA | Phascolarctobacterium sp. | 99.85% |
| 83 | 10 D5 FAA | Roseburia faecalis 1 | 99.84% |
| 84 | 9 D6 FAA | Roseburia faecalis 2 | 96.76% |
| 85 | 9A BHI | Roseburia hominis | 99.04% |
| 86 | 17 TSA | Roseburia intestinalis | 100% |
| 87 | 11 TSA | Roseburia sp. | 95.07% |
| 88 | 23 D5 FAA | Ruminococcus albus | 96.96% |
| 89 | 6 FAA NB SS | Ruminococcus bromii 1 | 100% |
| 90 | 17 FAA SS | Ruminococcus bromii 2 | 92.83% |
| 91 | 17 TSAB | Ruminococcus lactaris | 94.46% |
| 92 | 2 FAA NB | Ruminococcus luti | 98.91% |
| 93 | 15 TSA | Ruminococcus obeum | 99.06% |
| 94 | 4 FAA | Ruminococcus torques 1 | 99.27% |
| 95 | 11 FAA | Ruminococcus torques 2 | 100% |
| 96 | 8 D6 FAA SS | Ruminococcus torques 3 | 96.74% |
| 97 | 9B D6 FAA SS | Ruminococcus torques 4 | 91.94% |
| 98 | 13 FAA NB | Ruminococcus torques 5 | 91.47% |
| 99 | 5 BHI | Ruminococcus sp. 1 | 94.32% |
| 100 | 11 FAA NB | Ruminococcus sp. 2 | 98.04% |
| 101 | 4 D6 FAA SS | Ruminococcus sp. 3 | 97.05% |
| 102 | 4 FAA SS AER. | Staphylococcus epidermidis | 99.82% |
| 103 | 1 FAA NB SS | Streptococcus mitis | 100% |
| 104 | 11 FAA NB SS | Streptococcus thermophilus | 100% |
| 105 | 12 D6 FAA SS | Synergistes sp. | 95.83% |
| 106 | 16 D5 FAA | Turicibacter sanguinis | 100% |

[a]% ID for each species was determined using the 16S rRNA gene database, Green Genes. Average length of sequences used to obtain identification was 550 nucleotides. (Green Genes BLAST interface to 16 S data URL: http://areengenes.lbl.goviccii~bin/nph-blast interface.cgi)
[b]The strain Faecalibacterium prausnitzii 5 FAA NB requires Liquid Gold for growth. A 3% final volume of Liquid Gold produced from the chemostat where the donor fecal sample was cultured was used to supplement FAA plates. Growth was observed after 48 hours.
[c]Multiple strains of the same species are denoted by a number following the species name. For example, Clostridium aldenense 1 and 2 are two different strains of the same species. Shaded boxes indicate strains that are likely novel species (and in some cases, genera)

TABLE 3

Intestinal bacterial strains isolated and purified from donor stool in DEC-2. Closest species match, inferred by alignment of 16SrRNA sequence to GreenGenes database*

Acetobacterium sp.
Acidaminococcus intestinalis
Anaerostipes hadrus
Atopobium minutum
Bacteroides fragilis
Bacteroides ovatus
Bacteroides vulgatus
Bifidobacterium adolescentis
(2 different strains)
Bifidobacterium longum
(2 different strains)
Blautia coccoides
Blautia producta
Clostridium aldenense
Clostridium citroniae
Clostridium cocleatum
Clostridium hathewayi
Clostridium lactatifermentans
Clostridium orbiscindens
Collinsella aerofaciens
Dorea longicatena
(2 different strains)
Escherichia coli
Eubacterium desmolans
Eubacterium eligens
Eubacterium fissicatena
Eubacterium limosum
Eubacterium rectale
(4 different strains)
Eubacterium sp. (unclassified)
(3 different strains)
Eubacterium ventriosum
Faecalibacterium prausnitzii
Lachnospira pectinoshiza
Lactobacillus casei
Lactobacillus paracasei
Parabacteroides distasonis
Raoultella sp.
Roseburia faecalis TABLE 3-continued Intestinal bacterial strains isolated and
purified from donor stool in DEC-2.
Closest species match, inferred by alignment of
16SrRNA sequence to GreenGenes database*

Roseburia hominis
Roseburia intestinalis
Roseburia inulinivorans
Ruminococcus torques
(2 different strains)
Ruminococcus obeum
(2 different strains)
Streptococcus mitis

*Closest species match was inferred by alignment of 16S rRNA sequence to GreenGenes database;
note
that in some cases 16 S rRNA gene sequences could not resolve identity beyond genus, and that closest match does not infer definitive speciation. Shaded boxes indicate strains in DEC-2 that are NOT in DEC-1.

Liquid Gold can be stored at 4° C. for weeks at a time without losing its capacity to support microbial growth, indicating that Liquid Gold's ability to support or promote growth is stable and can be preserved for a prolonged period of time. Liquid Gold can also be frozen and preserved for future use.

In an embodiment, DEC-1 Liquid Gold is provided herein. In another embodiment, DEC-2 Liquid Gold is provided herein. In yet another embodiment, DEC-3 Liquid Gold is provided herein. In another embodiment, Native Liquid Gold is provided herein. It should be understood that Liquid Gold can be produced from culturing many different fecal samples and/or combinations of the human intestinal strains provided herein, and that such types of Liquid Gold are encompassed by the present invention. For example, Liquid Gold may be produced by culturing at least one, at least three, at least five, at least 8, at least 10, at least 15, or at least 25 of the bacterial strains listed in Table 1, Table 2 or Table 3. In an embodiment, Liquid Gold is produced by culturing all of the strains listed in Table 1, Table 2 or Table 3. In another embodiment, Liquid Gold is produced by culturing some of the strains listed in Table 1, Table 2 or Table 3.

In a further embodiment, methods of using Liquid Gold to support and/or enhance growth of microbes, e.g., human intestinal anaerobic microbes, are provided herein. In an embodiment, Liquid Gold is used to supplement standard laboratory culture media in a liquid culture, e.g., in a chemostat. For example, Liquid Gold may be added to culture media before culturing begins, or during culturing of microbes. Alternatively, Liquid Gold may be added to plates, e.g., solid media in a dish such as a petri dish, to support or enhance growth of microbes on the solid media. It will be understood that many variations are possible and are encompassed by the present invention.

In an embodiment, Liquid Gold is made by growing bacterial communities using the culture media referred to herein as "Media 1", prepared as follows:

Media 1 is prepared in the following steps (for 2 L):

Mixture 1: The following reagents are dissolved in 1800 mL of distilled water (ddH$_2$O): peptone water, 4 g (Oxoid Limited); Yeast extract, 4 g (Oxoid Limited); NaHCO$_3$, 4 g (Sigma); CaCl$_2$, 0.02 g (Sigma); Pectin (from citrus), 4 g (Sigma); Xylan (from beechwood), 4 g (Sigma); Arabinogalactan, 4 g (Sigma); Starch (from wheat, unmodified), 10 g (Sigma); Casein, 6 g (Sigma); inulin (from Dahlia tubers), 2 g (Sigma); NaCl, 0.2 g (Sigma). Water (ddH$_2$O) is added to 1900 mL, as the volume is reduced to 1800 mL after autoclaving. The mixture is sterilized by autoclaving at 121° C. for 60 min and allowed to cool overnight.

Mixture 2: The following reagents are dissolved in 100 mL of distilled water (Mixture 2A): K$_2$HPO$_4$, 0.08 g; KH$_2$PO$_4$, 0.08 g; MgSO$_4$, 0.02 g; Hemin, 0.01 g; Menadione, 0.002 g. Bile salts (1 g) is dissolved in 50 mL of distilled water (Mixture 2B). L-cysteine HCl (1 g) is also dissolved in 50 mL of distilled water (Mixture 2C). After Mixtures 2B and 2C dissolve they are added to Mixture 2A resulting in the formation of a fine white precipitate. This precipitate is then dissolved by the drop-wise addition of 6M KOH until a clear, brown solution is formed (Mixture 2). This mixture (200 mL total volume) is sterilized by filtering through a 0.22 μm filter.

Culture media ("Media 1"): Mixture 2 (0.2 L) is aseptically added to mixture 1 (1.8 L), in order to reach the final volume of 2 L. To prevent future foaming, 5 mL of antifoam B silicone emulsion (J. T. Baker) is aseptically added to each 2 L bottle of media.

In an embodiment, mucin is added to Media 1 (to make "Media 1+mucin"). In this embodiment, mixture 1 is prepared by adding 1600 mL of ddH$_2$O before autoclaving. The mucin addition is prepared by dissolving 8 g mucin (e.g., from porcine stomach, type II) in 200 mL of ddH$_2$O and autoclaved for 20 minutes. Mixture 2 is prepared as described above. After autoclaving, mixture 2 (0.2 L) and the mucin solution (0.2 L) are aseptically added to mixture 1 (1.6 L), in order to reach the final volume of 2 L. Again, 5 mL of antifoam B silicone emulsion is aseptically added to each 2 L bottle of media.

In another embodiment, Liquid Gold is made by growing bacterial communities using standard culture media, many of which are known in the art. In an embodiment, mucin is added to the culture media. For example, mucin may be added at a concentration of 1-10%, e.g., 4 g/L. The amount of mucin to be used will vary depending on culture conditions and is determined by the skilled artisan based on common general knowledge and routine methods.

In an embodiment, in order to produce Liquid Gold, a 10% w/v fecal slurry supernatant (referred to herein as a "10% inoculum) is cultured in a chemostat. In another embodiment, in order to produce Liquid Gold, a 20% w/v fecal slurry supernatant (referred to herein as a "20% inoculum) is cultured in a chemostat. In other embodiments, 5-25%, 5%, 10%, 15%, 20% or 25% inoculums are cultured in a chemostat, e.g., a single-stage chemostat system, to produce Liquid Gold. It should be understood that any % inoculum can be used to inoculate a chemostat vessel to produce Liquid Gold, as long as a sufficient amount of the fecal sample is present to seed the vessel, and the resulting fecal slurry is not too thick or viscous to work with.

In an embodiment, in order to produce Liquid Gold, a chemostat system is used where the growth medium is continuously fed into the chemostat vessel at a rate of 400 mL/day (16.7 mL/hour) to give a retention time of 24 hours, a value set to mimic the retention time of the distal gut (Cummings, J. H. et al., Gut (1976), 17:210-18). In another embodiment, the growth medium is continuously fed into the chemostat at a rate of about 148 mL/day (6.2 mL/hour) to give a retention time of 65 hours. In an embodiment, Liquid Gold is produced from a chemostat having a system retention time of about 20 to about 70 hours, about 20 hours, about 22 hours, about 24 hours, about 26 hours, about 28 hours, or about 30 hours, about 40 hours, about 50 hours, about 60 hours, about 65 hours, or about 70 hours.

We report herein that several novel bacterial species from the human gut have been cultured by supplementation of culture media with Liquid Gold (e.g., 3% v/v Liquid Gold). Several bacterial species have been isolated for the first time using the methods provided herein, including using Liquid Gold. In an aspect, there is provided herein a method of culturing *Faecalibacterium prausnitzii*, wherein the growth media is supplemented with Liquid Gold. In some embodiments, there is provided herein a method of culturing strains which have not been previously isolated, e.g., *Clostridium aldenense* 1, *Clostridium aldenense* 2, *Clostridium hathewayi* 1, *Clostridium hathewayi* 2, *Clostridium hathewayi* 3, *Clostridium thermocellum*, *Ruminococcus bromii* 2, *Ruminococcus torques* 4, *Ruminococcus torques* 5, *Clostridium cocleatum* (e.g., *Clostridium cocleatum* 21 FAA1), *Eubacterium desmolans* (e.g., *Eubacterium desmolans* 48FAA1), *Eubacterium limosum* 13LG, *Lachnospira pectinoshiza*, *Ruminococcus productus* (e.g., *Ruminococcus productus* 27FM), *Ruminococcus obeum* (e.g., *Ruminococcus obeum* 11FM1), *Blautia producta*, and/or *Clostridium thermocellum*, wherein the growth media is supplemented with Liquid Gold.

In an aspect, there are provided herein certain isolated bacterial strains, which have not been previously isolated. In an embodiment, there is provided herein an isolate of *Faecalibacterium prausnitzii*. In another embodiment, there is provided herein an isolate of *Clostridium aldenense* 1, *Clostridium aldenense* 2, *Clostridium hathewayi* 1, *Clostridium hathewayi* 2, *Clostridium hathewayi* 3, *Clostridium thermocellum*, *Ruminococcus bromii* 2, *Ruminococcus torques* 4, *Ruminococcus torques* 5, *Clostridium cocleatum* (e.g., *Clostridium cocleatum* 21 FAA1), *Eubacterium desmolans* (e.g., *Eubacterium desmolans* 48FAA1), *Eubacterium limosum* 13LG, *Lachnospira pectinoshiza*, *Ruminococcus productus* (e.g., *Ruminococcus productus* 27FM), *Ruminococcus obeum* (e.g., *Ruminococcus obeum* 11FM1), *Blautia producta*, or *Clostridium thermocellum*.

Culture conditions for exemplary bacterial strains isolated using methods provided herein are given in Table 4.

TABLE 4

Culture conditions for anaerobic strains isolated from a human fecal sample.

| Strain | Closest species | Colony morphology | Growth media used for synthetic stool preparations' | Relative growth rate2 |
| --- | --- | --- | --- | --- |
| 18 FAA | *Eubacterium rectale* | Small, white/translucent | FAA + 5% DSB | +++ |
| 10 FAA | *Dorea longicatena* | Small/medium, opaque, somewhat mucoid | FAA + 5% DSB | +++ |
| 42 FAA 1 | *Dorea longicatena* | Medium, opaque, pitting | FAA + 5% DSB | +++ |
| 31 FAA 1 | *Roseburia intestinalis* | Medium, opaque | FAA + 5% DSB + 3% LG | +++ |
| 6 MRS | *Lactobacillus casei/paracasei* | Medium, white, sticky | FAA + 5% DSB | +++ |
| 1 FAA | *Eubacterium rectale* | Pinpoint, opaque/white | FAA + 5% DSB | +++ |
| 27 FM | *Ruminococcus productus* | Small, white, dry | FAA + 5% DSB | + |
| 30 FAA | *Ruminococcus torques* | Small, white, dry | FAA + 5% DSB | +++ |
| 2 MRS | *Ruminococcus obeum* | Medium, white/opaque, sticky | FAA + 5% DSB | + |
| 6 FM 1 | *Eubacterium rectale* | Medium, white/opaque, sticky | FAA + 5% DSB + 3% LG | +++ |
| 2 FAA | *Bifidobacterium longum* | Small, brown, translucent, metallic sheen, sticky | FAA + 5% DSB | +++ |
| 39 FAA 1 | *Roseburia faecalis* | Medium, white/opaque, pitting | FAA + 5% DSB + 3% LG | +++ |
| 14 LG 2 | *Acidaminococcus intestinalis* | Large, white | FAA + 5% DSB | +++ |
| 5 FM | *Parabacteroides distasonis* | Small, white, translucent | FAA + 5% DSB | +++ |
| 21 FAA 1 | *Clostridium cocleatum* | Medium, white/opaque, very pitting/difficult to scrape, sticky | FAA + 5% DSB | +++ |
| 20 MRS 1 | *Bifidobacterium adolescentis* | Pin, brown/opaque, slight metallic sheen, sticky | FAA + 5% DSB | +++ |
| 48 FAA 1 | *Eubacterium desmolans* | Pinpoint, white/opaque, sticky | FAA + 5% DSB | + |
| 5 MM 1 | *Bacteroides ovatus* | Small, white/translucent | FAA + 5% DSB | +++ |
| 4 FM 1 | *Bifidobacterium longum* | Pinpoint, translucent, yellow, dry, pitting, metallic sheen, sticky | FAA + 5% DSB | +++ |

TABLE 4-continued

Culture conditions for anaerobic strains isolated from a human fecal sample.

| Strain | Closest species | Colony morphology | Growth media used for synthetic stool preparations[1] | Relative growth rate[2] |
|---|---|---|---|---|
| 11 FM 1 | Ruminococcus obeum | Small, white/opaque, translucent | FAA + 5% DSB | ++ |
| F1 FAA 1 | Eubacterium eligens | Pinpoint, pink/purple/opaque | FAA + 5% DSB + 3% LG | + |
| 25 MRS 1 | Lactobacillus casei | Small, white/opaque, sticky | FAA + 5% DSB | +++ |
| 13 LG | Eubacterium limosum | Small, off-white/opaque | FAA + 5% DSB + 3% LG | +++ |
| 9 FAA | Ruminococcus torques | Small, white/opaque, translucent | FAA + 5% DSB | +++ |
| 47 FAA | Eubacterium ventriosum | Sticky, small | FAA + 5% DSB | +++ |
| 3 FM 2 | Collinsella aerofaciens | Pinpoint, white/opaque, translucent, dry | FAA + 5% DSB | +++ |
| 11 FAA 1 | Bifidobacterium adolescentis | Small, yellow/opaque, mucoid | FAA + 5% DSB | +++ |
| 34 FAA 1 | Lachnospira pectinoshiza | Pinpoint, yellow | FAA + 5% DSB + 3% LG | ++ |
| 40 FAA | Faecalibacterium prausnitzii | Pinpoint, transparent | FAA + 3% LG | +++ |
| 29 FAA 1 | Eubacterium rectale | small, white/opaque, translucent | FAA + 5% DSB | +++ |

[1]FAA: Fastidious anaerobe agar, commercially available as Lab90; DSB: Defibrinated sheep blood, commercially available LG: Liquid Gold, a clarified, filtered effluent supernatant from chemostat communities seeded from healthy fecal communities, required by a number of synthetic stool strains for optimal growth.
[2]Relative growth rate; on average plates were incubated for 3 days at 37° C. under anaerobic conditions.

As used herein, "anaerobic" bacteria refers to bacteria which are facultatively anaerobic as well as bacteria which are strictly anaerobic.

As used herein, "standard culture media" refers to common and/or commercially available growth media for microorganisms, such as nutrient broths and agar plates, of which many variations are known in the art. Standard culture media generally contains at least a carbon source for bacterial growth, e.g., a sugar such as glucose; various salts which are required for bacterial growth, e.g., magnesium, nitrogen, phosphorus, and/or sulfur; and water. Non-limiting examples of standard culture media include Lysogeny broth (LB), A1 broth, and culture media described herein. Standard culture media for use in methods provided herein will be selected by a skilled artisan based on common general knowledge. The terms "standard culture media" and "standard laboratory culture media" are used interchangeably herein.

As used herein, the terms "pure isolate," "single isolate" and "isolate" are used interchangeably to refer to a culture comprising a single bacterial species or strain, e.g., grown axenically, in isolation from other bacterial species or strains.

For strains listed in the tables herein, the closest bacterial species was determined using the 16S rRNA full-length sequences, which were aligned with the NAST server (DeSantis, T. Z. Jr. et al., Nucleic Acids Res., 34:W394-W399 (2006)) and were then classified using the GreenGenes classification server (DeSantis, T. Z. Jr. et al., Appl. Environ. Microbiol., 72:5069-5072 (2006)), as described below. The most specific name in the GreenGenes classification was used and we report the DNA maximum likelihood score for each classification.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Materials and Methods

Single-stage Chemostats and Inoculation

We developed a single-stage chemostat vessel to model the human distal gut microbiota by modifying a Multifors fermentation system (Infors, Switzerland; shown in FIG. 1). Conversion from a fermentation system into a chemostat was accomplished by blocking off the condenser and bubbling nitrogen gas through the culture. The pressure build up forced the waste out of a metal tube (formerly a sampling tube) at a set height and allowed for the maintenance of a 400 mL working volume.

Throughout the duration of the experiment, the vessels were kept anaerobic by bubbling filtered nitrogen gas (Praxair) through the culture. Temperature (37° C.) and pH (set to 7.0; usually fluctuated around 6.9 to 7 in the culture) were automatically controlled and maintained by the computer-operated system. The system maintained the culture pH using 5% (v/v) HCl (Sigma) and 5% (w/v) NaOH (Sigma). The growth medium was continuously fed into the vessel at a rate of 400 mL/day (16.7 mL/hour) to give a retention time of 24 hours, a value set to mimic the retention time of the distal gut (Cummings, J. H. et al., Gut (1976), 17:210-18). Another retention time of 65 hours (−148 mL/day, 6.2 mL/hour) was also tested to determine the effect of retention time on the composition of the chemostat community.

Since the growth medium contained components which cannot survive sterilization by autoclaving (see below), the vessels were autoclaved with 400 mL of ddH$_2$O. During autoclaving, the waste pipes were adjusted so the metal tube reached the bottom of the vessel. Once the vessel cooled it was fitted to the rest of the computer operated unit, filtered nitrogen gas was bubbled through the water to pressurize and drain the vessel. The waste pipe was then raised to the working volume (400 mL) and 300 mL of sterile media was pumped into the vessel. The vessel was then left stirring, heating, and degassing overnight. To check for contamination within the vessel, each vessel was aseptically sampled and plated out (both aerobically and anaerobically) on fastidious anaerobe agar (FAA) supplemented with 5% defibrinated sheep blood. This procedure was repeated one day before inoculation and immediately prior to inoculation to ensure contamination was avoided.

Collection and Preparation of Fecal Inocula

Fresh fecal samples were provided by a healthy female donor (42 years old, with no history of antibiotic use in the 10 years prior to stool donation; "Donor 6") or by a healthy male donor (43 years old, with no history of antibiotic use in the 6 years prior to stool donation; "Donor 5"). Other donors also provided fecal samples (e.g., Donor 1, Donor 2, etc.). All donors were healthy subjects from 38 to 43 years of age with no recent history of antibiotic treatment. Research Ethics Board (REB) approval was obtained for fecal collection and use in these experiments.

To prepare the inoculum, freshly voided stool samples were collected and immediately placed in an anaerobic chamber (in an atmosphere of 90% N$_2$, 5% CO$_2$ and 5% H$_2$). A 10% (w/v) fecal slurry was immediately prepared by macerating 5 g of fresh feces in 50 mL of anaerobic phosphate buffered saline (PBS) for 1 minute using a stomacher (Tekmar Stomacher Lab Blender, made by Seward). The resulting fecal slurry was centrifuged for 10 minutes at 1500 rpm to remove large food residues. The resulting supernatant was used as the inoculum for this study. The 10% original w/v fecal slurry supernatant is referred to herein as the "10% inoculum". We also compared a 10% inoculum to a 20% (w/v) inoculum to determine whether any differences existed between these two concentrations. The 20% (w/v) inoculum was prepared in the same manner as the 10% inoculum except that 10 g of feces was added to 50 mL of anaerobic PBS prior to homogenization. Again, the inoculum derived from the 20% original w/v fecal slurry supernatant is referred to herein as the "20% inoculum".

Inoculation Process

To give a final working volume of 400 mL, 100 mL of 10% inocula was added to the 300 mL of sterile media in each vessel. Since the thickness of the fecal inoculum made it difficult to seed the vessel through the septum using a needle, the inoculum was added to the vessel through the waste pipe using a syringe. Immediately following inoculation the pH controls were turned on so the vessel pH was adjusted to and maintained at a pH of about 6.9 to 7.0. During the first 24 hours post-inoculation the communities were grown in batch culture to allow the community to adjust from in vivo to in vitro conditions and avoid culture washout. During this period the vessels were heated, degassed and stirred with continuous pH adjustment. After this 24 hour period the feed pumps were turned on and the vessels were run as chemostats. Fresh culture medium was added continuously and waste was continuously removed.

In the chemostat, culture conditions and media supply were maintained constant. The chemostat system was generally set with a retention time of 24 hours to mimic distal gut transit time.

Preparation of the Growth Medium

A culture growth medium for the chemostat was developed based on media used in previous studies attempting to mimic the human gut (Gibson, G. R. et al., Appl. Environ. Microbiol., 54(11):2750-5, 1988; Lesmes, U. et al., J. Agric. Food Chem., 56: 5415-5421, 2008). Due to the large amount of medium used by each vessel, medium was prepared in 2 L volumes. The culture medium was prepared in the following steps (for 2 L):

Mixture 1: The following reagents were dissolved in 1800 mL of distilled water (ddH$_2$O): peptone water, 4 g (Oxoid Limited); Yeast extract, 4 g (Oxoid Limited); NaHCO$_3$, 4 g (Sigma); CaCl$_2$, 0.02 g (Sigma); Pectin (from citrus), 4 g (Sigma); Xylan (from beechwood), 4 g (Sigma); Arabinogalactan, 4 g (Sigma); Starch (from wheat, unmodified), 10 g (Sigma); Casein, 6 g (Sigma); inulin (from Dahlia tubers), 2 g (Sigma); NaCl, 0.2 g (Sigma). Water (ddH$_2$O) was added to 1900 mL, as the volume is reduced to 1800 mL after autoclaving. The mixture was sterilized by autoclaving at 121° C. for 60 min and allowed to cool overnight.

Mixture 2: The following reagents (all purchased from Sigma) were dissolved in 100 mL of distilled water (Mixture 2A): K$_2$HPO$_4$, 0.08 g; KH$_2$PO$_4$, 0.08 g; MgSO$_4$, 0.02 g; Hemin, 0.01 g; Menadione, 0.002 g. Bile salts (1 g) was dissolved in 50 mL of distilled water (Mixture 2B). L-cysteine HCl (1 g) was also dissolved in 50 mL of distilled water (Mixture 2C). After Mixtures 2B and 2C dissolved they were added to Mixture 2A resulting in the formation of a fine white precipitate. This precipitate was then dissolved by the drop-wise addition of 6M KOH until a clear, brown solution was formed (Mixture 2). This mixture (200 mL total volume) was sterilized by filtering through a 0.22 µm filter.

Culture media ("Media 1"): Mixture 2 (0.2 L) was aseptically added to mixture 1 (1.8 L), in order to reach the final volume of 2 L. To prevent future foaming, 5 mL of antifoam B silicone emulsion (J. T. Baker) was aseptically added to each 2 L bottle of media. The media was stored at 4° C. until use for a maximum of two weeks. A bit of media was plated out on FAA (aerobically and anaerobically) the day before adding to chemostat and immediately after taking off the chemostat, to check for contamination.

The media was pumped into each vessel using a peristaltic pump whose speed is controlled by the computer-operated system. To pump media from the bottles into the vessel, standard GL-45 glass bottle lids (VWR) had holes drilled into them to fit two stainless steel metal tubes. When Mixture 1 was prepared, the media bottle had all the required silicone tubing and 0.22 µm filters attached (see FIG. 1).

Each vessel was fed from one media bottle with a 2 L volume of media. Since the tubing which supplied the media to the vessel was also changed as each media bottle was changed, this helped to prevent back-growth of bacteria from the vessel into the sterile media reservoir. Each media bottle was plated out on supplemented FAA and grown both aerobically and anaerobically before each bottle was added to the chemostat and after each bottle was removed from the chemostat.

We compared our culture media (Media 1) to a media previously described in the literature (Walker, A. W. et al., Appl. Environ. Microbiol., 71 (7): 3692-700, 2005), since pH and peptide supply can alter bacterial populations and short-chain fatty acid ratios within microbial communities from human colon. This media was prepared using a similar method as was used to prepare our media, only the composition of the two mixtures changed. The chemostat media described in Walker et al. was prepared in the following steps (for 2 L):

Mixture 1: The following reagents were dissolved in 1800 mL of distilled water: peptone water, 12 g; $NaHCO_3$, 6.4 g; pectin (from citrus), 1.2 g; xylan (from beechwood), 1.2 g; arabinogalactan, 1.2 g; starch (wheat, unmodified), 10 g; casein hydrolysate, 12 g; amylopectin, 1.2 g. This mixture was sterilized in an autoclave at 121° C. for 60 min.

Mixture 2: L-cysteine HCl (1 g) was dissolved in 100 mL of distilled water (Mixture 2A). Bile salts (1 g) were dissolved in 100 ml of distilled water (Mixture 2B). Mixture 2B was added to Mixture 2A resulting in the formation of a fine white precipitate. The pH of the solution was then adjusted by the drop-wise addition of 6M KOH until a clear, colourless solution was formed. This mixture (200 mL total volume) was sterilized by filtering through a 0.22 µm filter.

Chemostat media: Mixture 2 (0.2 L) was aseptically added to mixture 1 (1.8 L), in order to reach the final volume of 2 L. To prevent future foaming, 5 mL of antifoam B silicone emulsion was aseptically added to each 2 L bottle of media. The media was stored at 4° C. until use for a maximum of two weeks.

To determine whether the addition of mucin to our culture media (Media 1) had an effect on the composition and structure of healthy distal gut communities, we compared one vessel fed with our culture media (without mucin) to two vessels fed with our culture media (containing mucin). The chemostat media with mucin was prepared in a similar manner as our culture media without mucin, with a couple of changes. Firstly, mixture 1 was prepared by adding 1600 mL of $ddH_2O$ before autoclaving. The mucin addition was prepared by dissolving 8 g mucin (from porcine stomach, type II) in 200 mL of $ddH_2O$, and autoclaved for 20 minutes. Mixture 2 was prepared as described above. After autoclaving, mixture 2 (0.2 L) and the mucin solution (0.2 L) were aseptically added to mixture 1 (1.6 L), in order to reach the final volume of 2 L. Again, 5 mL of antifoam B silicone emulsion was aseptically added to each 2 L bottle of media. The media was also stored at 4° C. until use for a maximum of two weeks.

Sampling

Each chemostat vessel was sampled daily by removing 4 mL of culture through the septum using a sterile needle and syringe. Samples were transferred into two screw-capped tubes which were stored at −80° C. to archive. During weekdays, 10 drops of antifoam B silicone emulsion was added through the septum by a syringe and needle at 9 am and 5 pm (20 drops per day total). On weekends, 20 drops of antifoam was added to each vessel around 12 pm. This amount of antifoam added to each vessel daily (in conjunction with the amount of antifoam present in the media) was sufficient to prevent foaming in our system using a 24 hour retention time.

DNA Extraction

The DNA used for DGGE analysis was extracted using a protocol involving a combination of bead beating, the Omega Bio-Tek E.Z.N.A.® Stool DNA Kit, and the Promega Maxwell®16 DNA Purification Kit. The first half of the protocol follows the June 2009 revision of the E.Z.N.A.® Stool DNA Kit protocol with a few alterations. Briefly, we added 200 µL of liquid chemostat or fecal sample, 300 µL of SLX buffer from the E.Z.N.A. kit, 10 µL of 20 mg/mL proteinase K (in 0.1 mM $CaCl_2$) and 200 mg of glass beads to a screw-capped tube and bead beat for 4×45 seconds (3 minutes total). The samples were then incubated at 70° C. for 10 minutes, 95° C. for 5 minutes and on ice for 2 minutes. Next we added 100 µL of Buffer P2 from the E.Z.N.A. kit to each tube and vortexed them for 30 seconds. This was followed by incubation on ice for 5 minutes and centrifugation at 14500×g for 5 minutes. The supernatant was then transferred into a new 1.5 mL tube and 200 µL of HTR reagent from the E.Z.N.A. kit was added to each tube using wide bore tips. The samples were then vortexed for 10 seconds and incubated at room temperature for 2 minutes. The tubes were then centrifuged at 14500×g for 2 minutes and the supernatant was transferred into Maxwell cartridges. The remainder of the DNA extraction protocol was carried out as described in the Maxwell®16 DNA Purification Kit protocol (Promega).

PCR and DGGE

The V3 region (339-539 bp, *Escherichia coli* numbering) of the 16S rRNA gene was amplified using primers HDA1 and HDA2-GC (Walter, J. et al., Appl. Environ. Microbiol., 66(1): 297-303, 2000). The PCR master mix consisted of Tsg DNA polymerase (Bio Basic) and 1× Thermopol buffer (with 2 mM $MgSO_4$, NEB), using DNA (extracted as described above) as a template. The cycling conditions were as follows: 92° C. for 2 min (92° C. for 1 min, 55° C. for 30 sec, 72° C. for 1 min)×35; 72° C. for 10 min. Three identical 50 µL PCR reactions were set up for each sample using 2 µL of DNA template. Each sample was concentrated using the EZ-10 Spin Column PCR Products Purification Kit (Bio Basic) by loading all three PCR reactions from each sample onto the same column and eluting in 45 µL of warm HPLC grade water. Once the PCR reactions were concentrated 10 µL of DGGE loading dye (0.05 g bromophenol blue in 10 ml 1×TAE) was added to each sample.

A DGGE ladder created from five laboratory strains was used to normalize the gel. This ladder consisted of V3 DGGE PCR reactions from laboratory strains 1/2/53 (*Coprobacillus*), 30/1 A (Enterococcaceae), 5/2/43 FAA (*Veillonella*), 1/1/41 A1 FAA CT2 (Peptostreptococcaceae), and 7/6/55B FAA (*Propionibacterium*). DNA from these strains was extracted using the method described by Strauss et al. (Strauss, J. et al., Anaerobe, 14(6): 301-9, 2008). The PCR reactions used to generate the amplicons to construct the ladder were prepared as described above, except 1 PCR reaction was prepared per stain. The five different PCR reactions were pooled and 62.5 µL of DGGE loading dye was added to the mixture.

The protocol used for DGGE analysis was developed based on a protocol using the DCode System (Bio-Rad Laboratories, Hercules, Calif., USA) described by Muyzer et al. (Muyzer, G. et al., Antonie Van Leeuwenhoek, 73(1): 127-41, 1998). 40 µL of the PCR/dye mixture was loaded onto each lane of the gel. The polyacrylamide gels consisted of 8% (v/v) polyacrylamide (37.5:1 acrylamide/bisacrylamide) in 0.5×TAE (TAE is Tris base, acetic acid and EDTA buffer, made using the following recipe: Tris base [tris (hydroxymethyl)aminomethane] (0.048% w/v); glacial acetic acid (17.4M) (0.011% v/v); EDTA disodium salt (0.0037% w/v)). The amplicons were separated using a denaturating gradient of 30-55%. Electrophoresis was performed in 0.5×TAE buffer at a constant temperature of 60° C. for 5 h at 120 V. Gels were stained for 10 minutes in ethidium bromide solution (in 1×TAE, Sigma Aldrich) and destained for 10 minutes in $ddH_2O$. Images were captured using the SynGene G-Box gel documentation system and GeneSnap software (version 6.08.04). The gels were normalized for saturation while the images were captured.

DGGE Statistical Analyses

DGGE gel images were analyzed using the Syngene GeneTools software (version 4.01.03, Perkin Elmer). The image background was subtracted using rolling disc subtraction with a radius of 30 pixels. Lanes were manually detected and set on each gel image.

Analysed bands were both automatically and manually detected for each profile. The profiles were matched using the "profile" type under the matching parameters menu with a set tolerance of 1%. Dendrograms were drawn using the Unweighted Pair Group Method with Arithmetic Mean (UPGMA). Profile comparison resulted in an automatically generated similarity matrix and dendrogram. Similarity index values range from 0 to 1, with values of 0 indicating two profiles have no bands in common, while values of 1 indicate the two profiles have identical banding patterns. Percent similarity values were calculated by multiplying the similarity index value by 100.

Comparing Two Vessels on Day (x): The similarity of two vessels was determined plotting the % similarity of V(x) vs. V(y) against the day the sample was taken. This analysis was carried out for samples taken every two days beginning at Day 0.

Figure 13A:
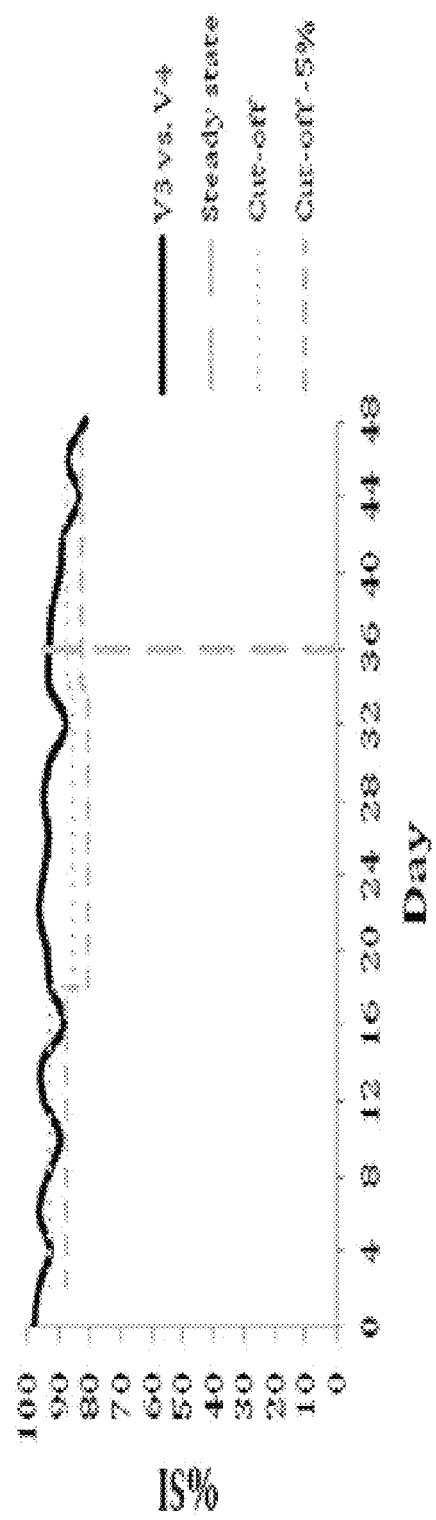
FIGS. 13A-F show community analysis of two identical chemostat vessels modeling the human distal gut. Each vessel was seeded with identical fecal inocula prepared from the feces of a healthy donor (donor 5). Parameters were calculated by analyzing DGGE patterns of general Bacteria (V3 region of the 16S gene) using GeneTools statistical analysis software. Samples were analyzed every two days throughout the duration of the experiment (days 0-48). The vertical dashed line represents the beginning of steady state conditions. A: Correlation coefficients (expressed as percentages) comparing the profiles of each vessel at the same time point, plotted over the course of the experiment. The horizontal dotted line represents the cut-off threshold calculated by comparing the similarity of identical marker lanes run on a single DGGE gel. The horizontal dashed line represents the cut-off threshold −5% and allows for a 5% difference in similarity between the profiles of each vessel. Up until day 48, both vessels were able to maintain very similar DGGE profiles. B: Correlation coefficients comparing the profiles of samples taken from each vessel over the course of the experiment to its starting inocula. The horizontal dotted line represents the cut-off threshold and the horizontal dashed line represents the cut-off threshold −5%. While the steady state community was different from the starting inoculum, the similarity was relatively consistent over time. C: Community dynamics as shown using moving window correlation analysis. Variability of the community within each vessel was calculated by comparing the profile of day (x) and day (x−2). The horizontal dotted line represents 100-(cut-off threshold) and the horizontal dashed line represents 100-(cut-off threshold −5%). By day 36 the communities within both vessels had reached steady state (when confirmed by visual inspection of the DGGE profiles between vessels). D: Shannon Diversity Index (H) plot representing the corrected community diversity of each vessel over the course of the experiment. The horizontal dotted line represents the average Shannon diversity index value of the starting inocula. The diversity in both vessels was similar to each other, stable over time, and similar to that of the starting inocula. E: Community richness (S) plot represented by plotting the number of corrected observed bands in each DGGE gel against time. The horizontal dotted line represents the average richness value of the starting inocula. The richness in both vessels was similar to each other, stable over time, and similar to that of the starting inocula. F: Shannon equitability index ($E_H$) plot representing the corrected community evenness values from each vessel over the course of the experiment. The horizontal dotted line represents the average Shannon equitability index value of the starting inocula. The evenness in both vessels was similar to each other, stable over time, and similar to that of the starting inocula.
Figure 13B:
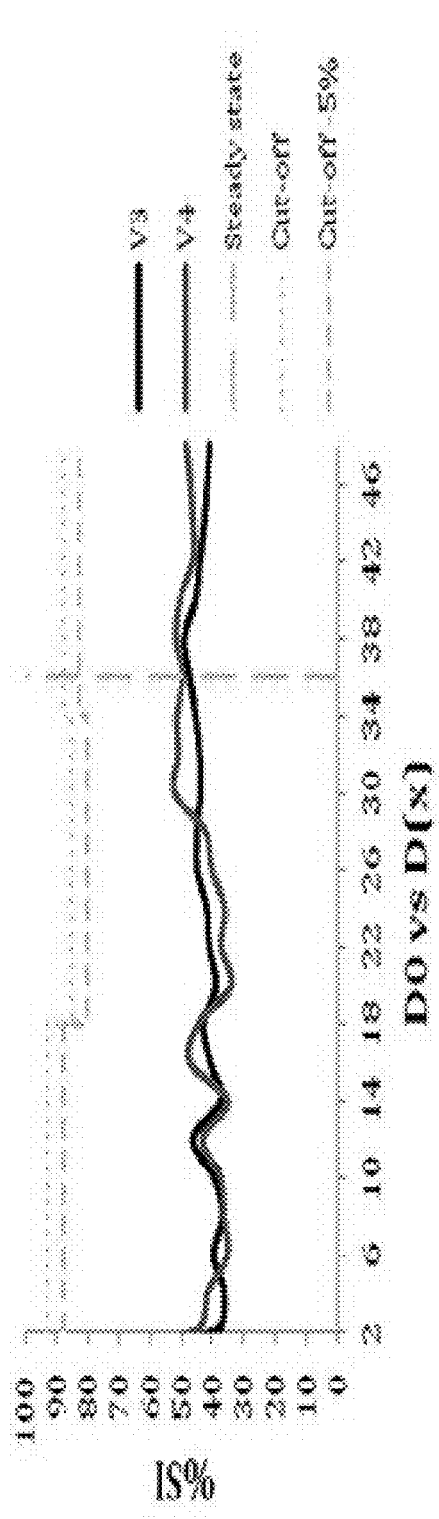
Figure 13C:
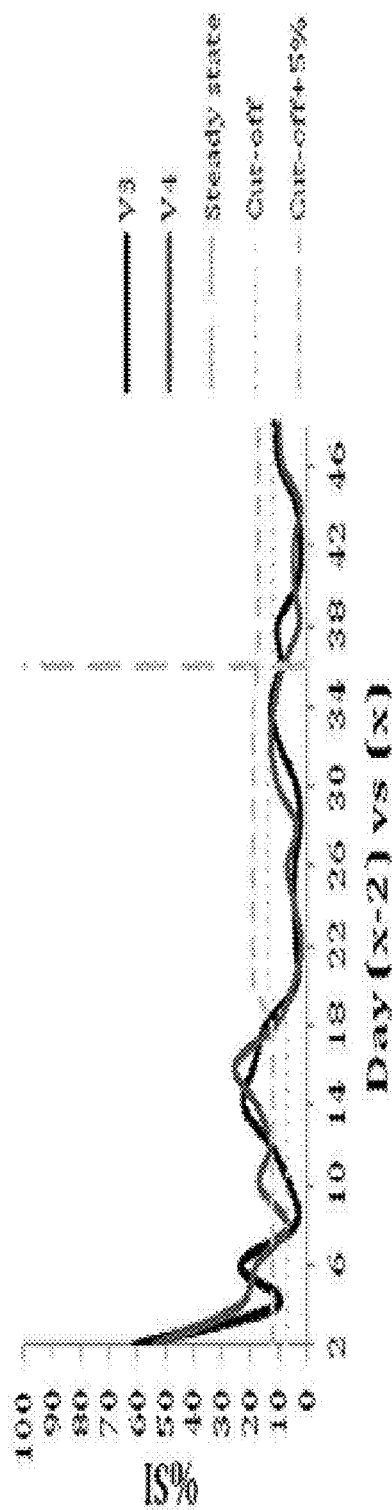
Figure 13D:
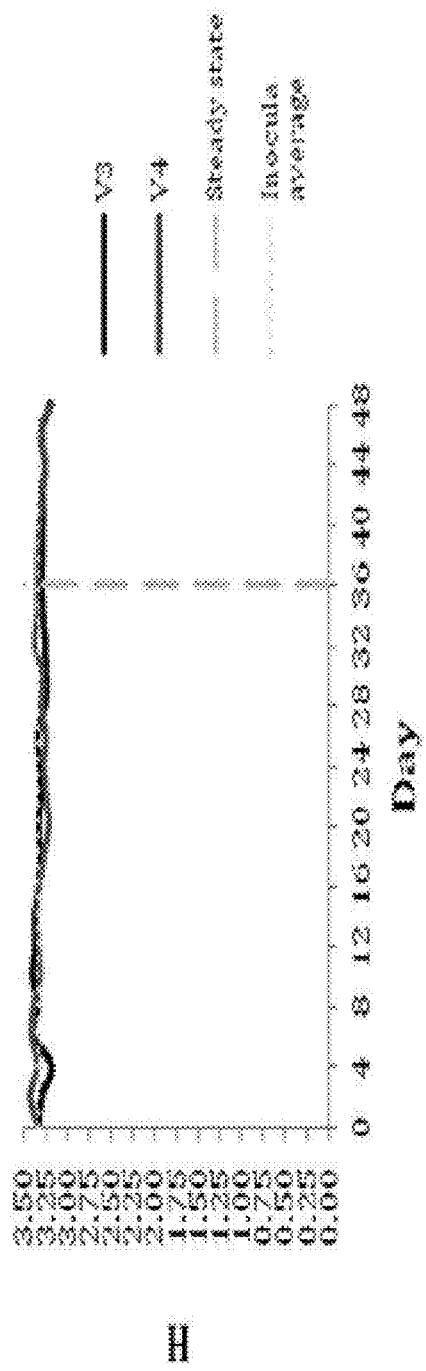
Figure 13E:
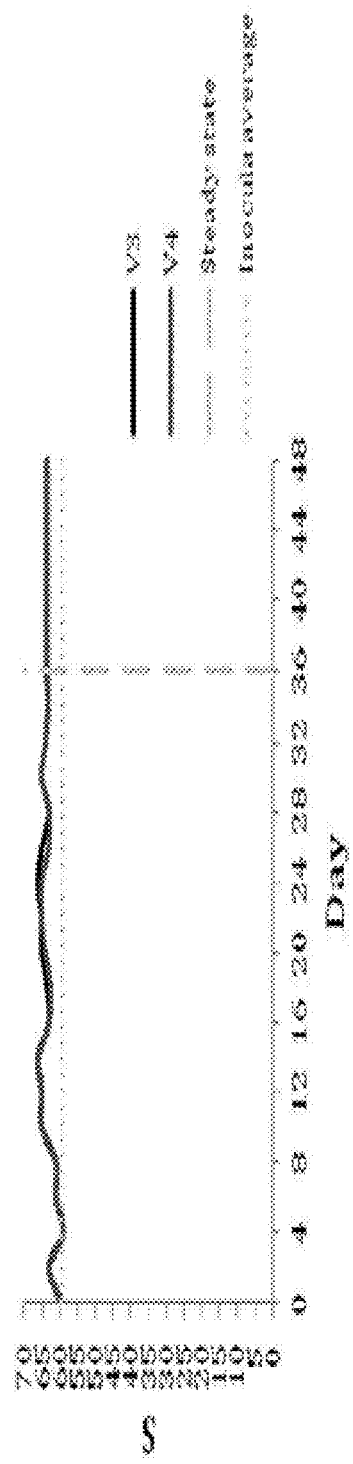
Figure 13F:
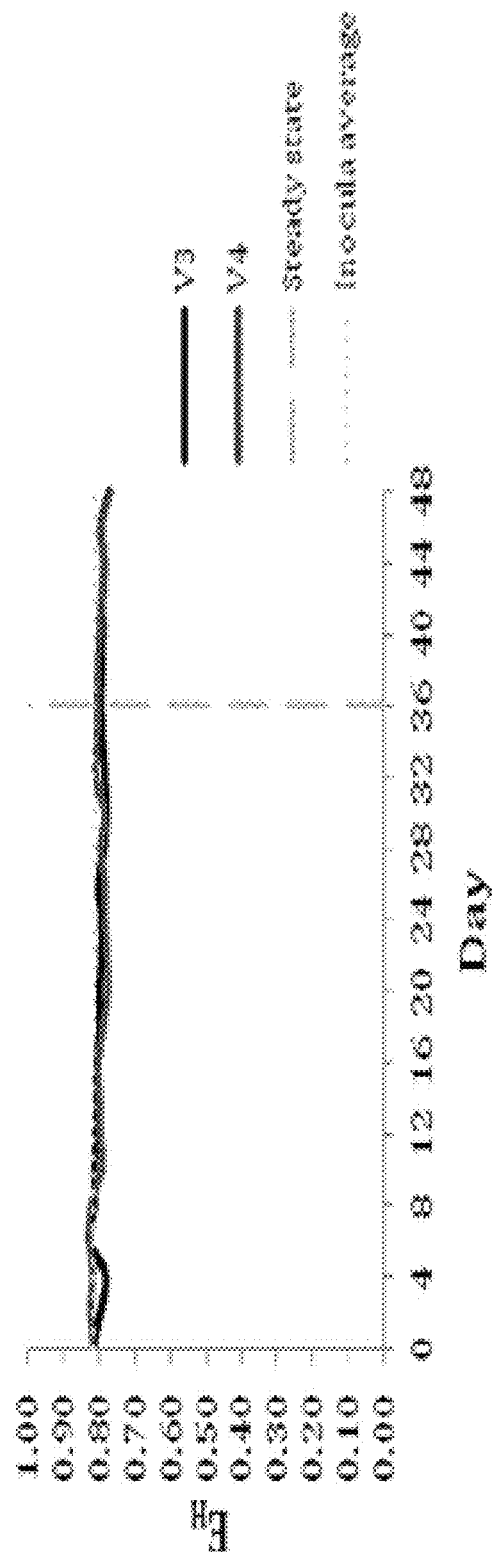

Community Dynamics: Community dynamics represents the changes within a community over a fixed time frame. Moving window analysis was performed by plotting the % similarity between consecutive sampling points. In this case we chose to plot Day (x−2) vs. Day (x). We found that this time interval was adequate and did not cause us to miss large fluctuations in the community dynamics and was in agreement with previous literature (Possemiers, S. et al., FEMS Microbiol. Ecol., 49(3): 495-507, 2004). This analysis resulted in the generation of a graph which was used to assess the stability of the community as well as to determine how long it took the vessel to reach steady state. An example of a moving window correlation plot illustrating community dynamics is shown in FIG. 13c.

The rate of change (Δt) can then be calculated as 100−the average of the respective moving window curve data points (Marzorati, M. et al., Environ. Microbiol., 10(6): 1571-81, 2008). The larger the change between the profiles of the consecutive sampling points the higher the Δt value. However, since an initial stabilization period is noted as the community transitions from an in vivo to an in vitro environment, values may vary depending on the period chosen (Marzorati, M. et al., Environ. Microbiol., 10(6): 1571-81, 2008). According to two papers by Wittebolle et al. (Marzorati, M. et al., Environ. Microbiol., 10(6): 1571-81, 2008; Wittebolle, L. et al., J. Appl. Microbiol., 107(2):385-94, 2009), a low Δt value ranges from 0-5%, a medium value ranges from 5-15%, and a high value is 15+%. Steady state is reached once the curve of the graph remains above the set threshold. We considered our chemostat communities to be stable (at steady state) once a low Δt value (0-5%) was maintained by the community.

Shannon Diversity Index

The Shannon index is a commonly used mathematical measure of community diversity which takes into account both species richness (number of species present) and evenness (relative species abundance). The Shannon diversity index (H') is calculated as shown below (Marzorati, M. et al., Environ. Microbiol., 10(6): 1571-81, 2008):

$$H' = -\sum_{i=1}^{S}(p_i \ln p_i)$$

where:
H'=the value of the Shannon diversity index
$p_i$=the proportion of the ith species
ln=the natural logarithm of $p_i$
s=total number of species in the community (richness)
Σ=sum from species 1 to species s.

The minimum value of the Shannon index is zero, which is equal to the value of H' for a community with a single species (i.e., a monoculture with no diversity). The H' value increases as community richness and evenness increase. Because of this, an increase in H' may be the result of an increase in species richness, an increase in species evenness, or an increase in both. This is a flaw in the index and the reason that care should be taken when using this measure of diversity. H' values have been found to range from 1.5 (low species richness and evenness) to 3.5 (high species evenness and richness) in natural systems (MacDonald, G. M., 2003, Biogeography: Space, Time and Life, John Wiley & Sons, Inc., U.S.A., pg 409). However, we find it more important to use the Shannon index to measure and track changes in the diversity of samples as compared to the original fecal inoculum (Gafan, G. P. et al., J. Clin. Microbiol., 43(8): 3971-8, 2005).

Range-weighted Richness

Range-weighted richness (Rr) is a measure of community richness that takes the percentage of denaturant needed to describe the diversity of the community into account when analyzing DGGE gels (Marzorati, M. et al., Environ. Microbiol., 10(6):1571-81, 2008). Rr is calculated as shown below:

$$Rr = N^2 \times D_g$$

where:
Rr=Range-weighted richness
N=total number of bands in the pattern
$D_g$=denaturing gradient comprised between the first and last band of the pattern.

Low Rr values are less than 10, medium Rr values range from 10 to 30, and high Rr values are greater than 30 (Marzorati, M. et al., Environ. Microbiol., 10(6):1571-81, 2008).

Shannon's Equitability

Community evenness is the degree to which the numbers of individuals are evenly divided between the different species of the community. Community evenness can be assessed by calculating Shannon's equitability ($E_H$; Marzorati, M. et al., Environ. Microbiol., 10(6): 1571-81, 2008). $E_H$ is calculated by dividing Shannon index (H') by $H_{max}$ (where $H_{max}$ is lnS). This is shown below as follows:

$$E_H = H'/H_{max} = H'/\ln S$$

$E_H$ values range from 0-1, with a value of 0 representing complete community unevenness and a value of 1 representing complete community evenness. Increases in the evenness result in an increase in community diversity (Pielou, E. C. 1975. Ecological diversity. Wiley, New York).

Example 1

Threshold for DGGE Analysis

A study by Possemiers et al. (Possemiers, S. et al., FEMS Microbiol. Ecol., 49(3):495-507, 2004) established a threshold stability criterion of 80% similarity (or 20% variability) for DGGE studies based on within-gel variability seen between identical marker lanes. According to this study, the threshold can be used in conjunction with moving window correlation analysis to monitor the dynamics of the community. This approach allows us to examine the similarity of a vessel to itself over time. The 80% similarity threshold can then be used to determine how long it takes a vessel to rise above this cut-off and reach steady state.

In order to apply this threshold to our studies, a similar analysis was carried out on the marker lanes from our DGGE gels. We found an average of 80.4±8.9% similarity, or 19.6±8.9% variability, between these marker lanes. Since these values correspond well with the values used in the Possemiers et al. study, a threshold of 80% similarity was also used for our analyses. In some cases individual within gel variation was used as a cut-off.

In the Examples below, we analyzed the colonization process in two identical vessels to determine whether these vessels can be run in parallel and still maintain identical communities. We also compared different concentrations of fecal inocula, different compositions of media, and different system retention times to optimize the operation of our chemostat system.

Example 2

Comparison of Same Donor Over Time

Figure 2:
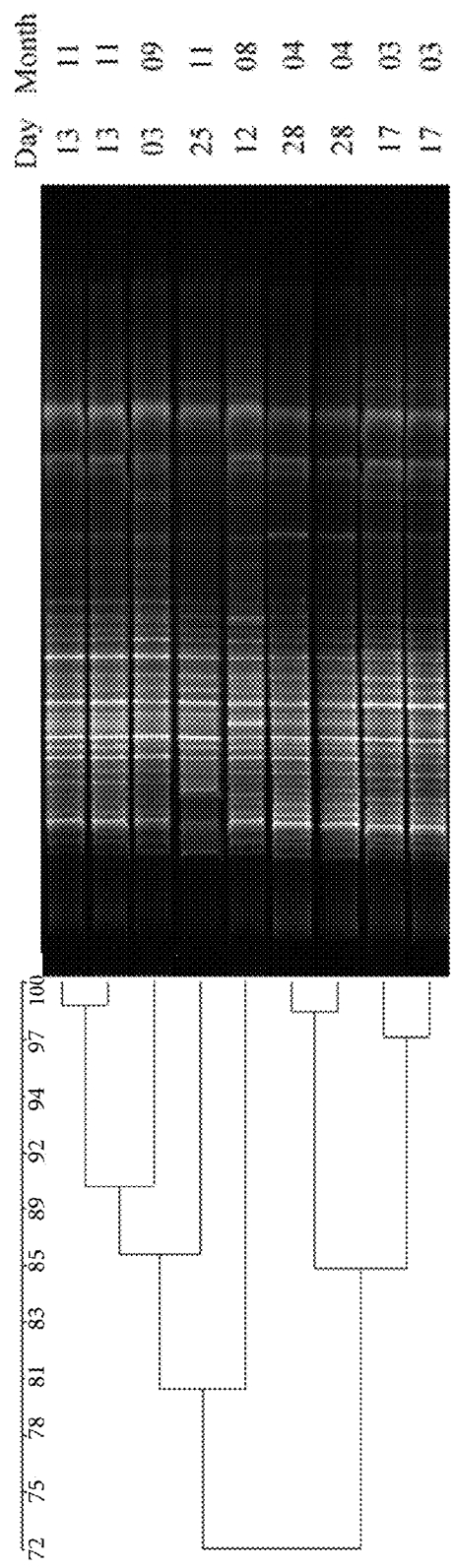
FIG. 2 shows a clustering Tree based on Dice similarity coefficient and Unweighted Pair Group Method with Arithmetic Mean (UPGMA) correlation of the DGGE profiles showing the 10% fecal inocula prepared from Donor 2 feces on several different donations over an 8 month period. The predominant bacterial species from this healthy donor remained stable over time.

The DGGE pattern of 10% inocula from Donor 2 (a 38-year old healthy female) over an 8 month period is shown in FIG. 2. As seen by visual inspection, the variation in the profiles seems to be due to differences in band brightness, not the appearance or disappearance of bands. The inocula isolated from this donor had an average correlation coefficient of 76.9±8.7%. Slight differences between profiles were shown in FIG. 2 where samples showed slightly higher similarity depending on the time of sample collection. Overall, the gut microbiota of this healthy donor remained stable over time.

The gut microbiota of this donor maintained a high diversity over time, with an average Shannon-Weaver index value of 3.39±0.08. The donor's microbiota also maintained a very high average range-weighted richness at 776.5±27.7. Finally, the community evenness was stable over time, with an average Shannon equitability value of 0.82±0.02.

Example 3

Comparison of Different Donors

Figure 3:
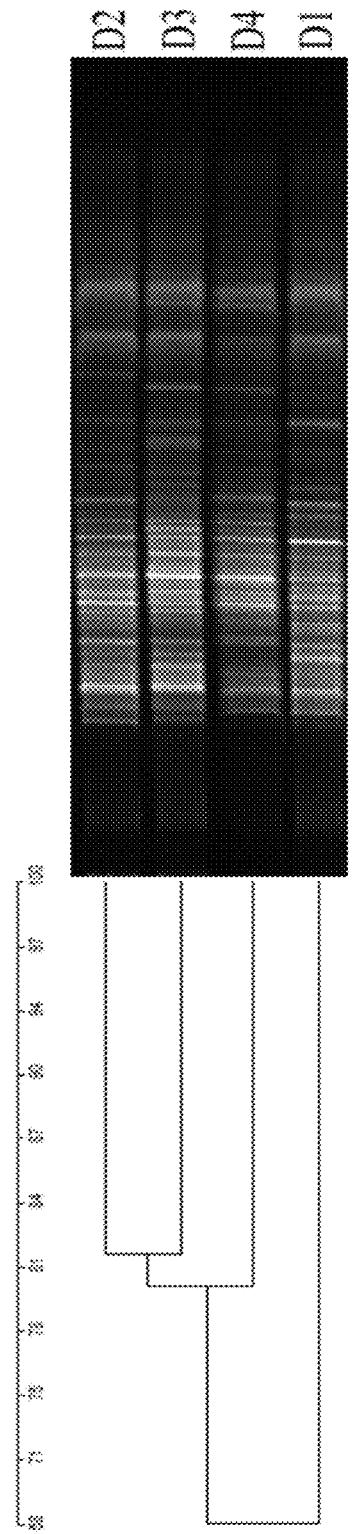
FIG. 3 shows a clustering Tree based on Dice similarity coefficient and UPGMA correlation of the DGGE profiles showing the 10% fecal inocula prepared from four different donors (donors 1-4). Each donor had a unique profile, with the profiles from some donors more similar to each other than others (e.g., Donors 2 and 3).

We used DGGE to compare fecal inocula isolated from four different healthy donors (from 38 to 43 years of age with no recent history of antibiotic treatment) (FIG. 3). We found that the fecal community of each donor was different from the communities of other individuals (as expected, Tannock, G. W., Eur. J. Clin. Nutr., 56 Suppl. 4:S44-9, 2002). The average correlation coefficient between the inocula from different donors was 74.4±8.4%.

The gut microbiota of all four donors had high diversity, with an average Shannon-Weaver index value of 3.42±0.04. The donor microbiota also maintained a very high average range-weighted richness at 585.3±26.2. The community evenness between the different donors was quite similar, with an average Shannon equitability value of 0.86±0.01.

We also used DGGE to compare two different communities, seeded by fecal samples from two different healthy donors, each of whom donated on at least two separate occasions. Donor 5 made two donations, about 5 months apart: "Run 20" was inoculated on Oct. 28, 2011, and "Run 22" was inoculated on Mar. 23, 2012. Donor 6 made two donations about 6 months apart: "Run 16" was inoculated on Feb. 10, 2011, and "Run 19" was inoculated on Aug. 3, 2011. We asked how similar are the inocula from the two different donors to each other; whether we would see the same loss of diversity from each donor; and how different are the two donors from each other.

Figure 10:
FIG. 10 depicts DGGE profiles comparing fecal communities to the communities present in the chemostat vessels immediately following inoculation. Two different chemostat runs were compared for each healthy donor (Donors 5 and 6). The fecal inocula used to seed the chemostat vessels was very similar to the starting fecal donation and not altered significantly by the process of preparing the inoculum.
Figure 11:
FIG. 11 depicts DGGE profiles comparing fecal communities from two different healthy donors (Donors 5 and 6). Each donor provided a sample on two different occasions. Donors 5 and 6 had different DGGE profiles. The DGGE profiles from both donors were consistent between donations.
Figure 12:
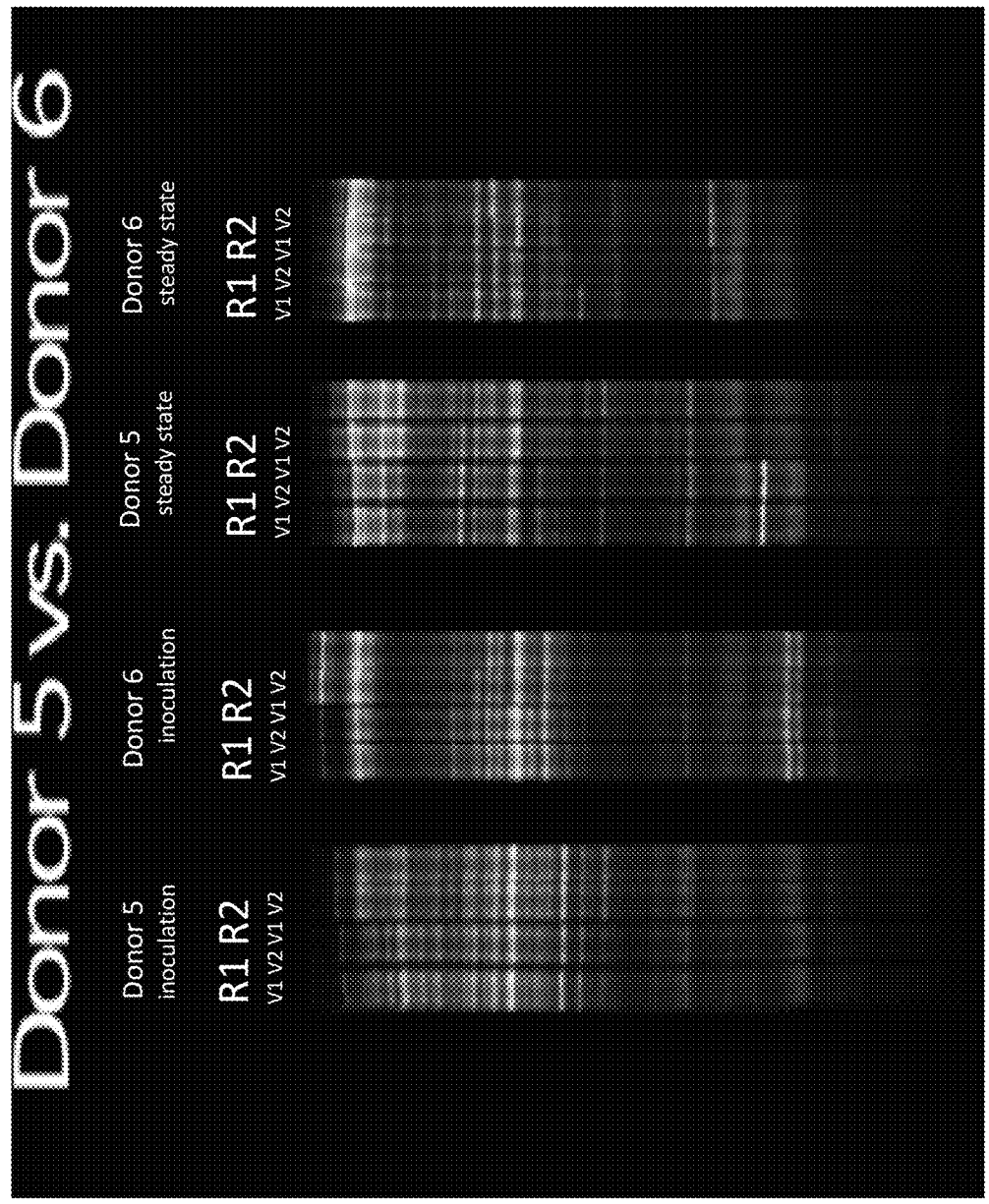
FIG. 12 depicts DGGE profiles comparing fecal communities present in the chemostat vessels immediately following inoculation to the steady state communities (samples obtained 36 days post-inoculation) for two different healthy donors (donors 5 and 6). Two different vessels were seeded with identical fecal inoculum for each chemostat run and two different chemostat runs were compared for each healthy donor. By DGGE, the fecal inocula from the same donor on two different occasions were more similar to each other than to fecal inocula from the other donor. Also, the steady state communities seeded with feces from the same donor were more similar to each other between chemostat runs than to the communities seeded with feces from another donor.

Results are shown in FIGS. 10-13. FIG. 10 shows that fecal inocula used to seed the chemostat vessels was very similar to the starting fecal donation, and not altered significantly by the process of preparing the inoculum. FIG. 11 shows that DGGE profiles from Donors 5 and 6 were consistent between donations. FIG. 12 shows that, by DGGE, the fecal inocula from the same donor on two different occasions were more similar to each other than to fecal inocula from another donor. Also, the steady state communities seeded with feces from the same donor were more similar to each other between chemostat runs than to communities seeded with feces from another donor. FIG. 13 shows that evenness in two vessels with the same inocula was similar to each other, stable over time, and similar to that of the starting inocula.

Example 4

Comparison of 10% Vs. 20% Inocula

Figure 4:
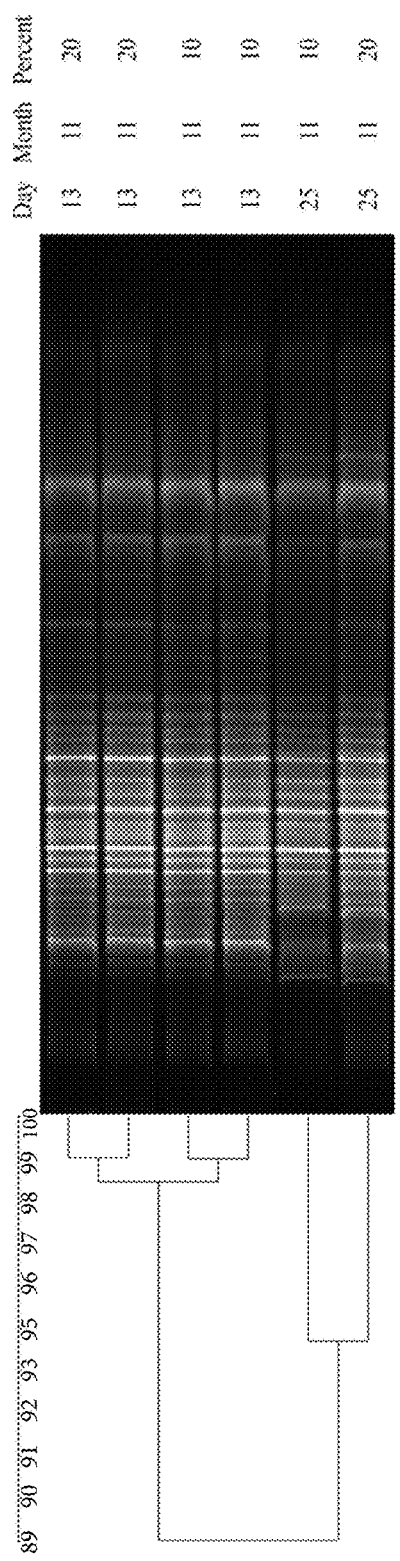
FIG. 4 shows a clustering Tree based on Dice similarity coefficient and UPGMA correlation of the DGGE profiles showing the 10% vs. 20% fecal inocula prepared from Donor 2 feces on two different donations. The 10% and 20% inocula were very similar to each other, therefore justifying the use of the 10% inocula (which requires less fecal donation and is easier to administer to the chemostat vessel upon inoculation).
Figure 5A:
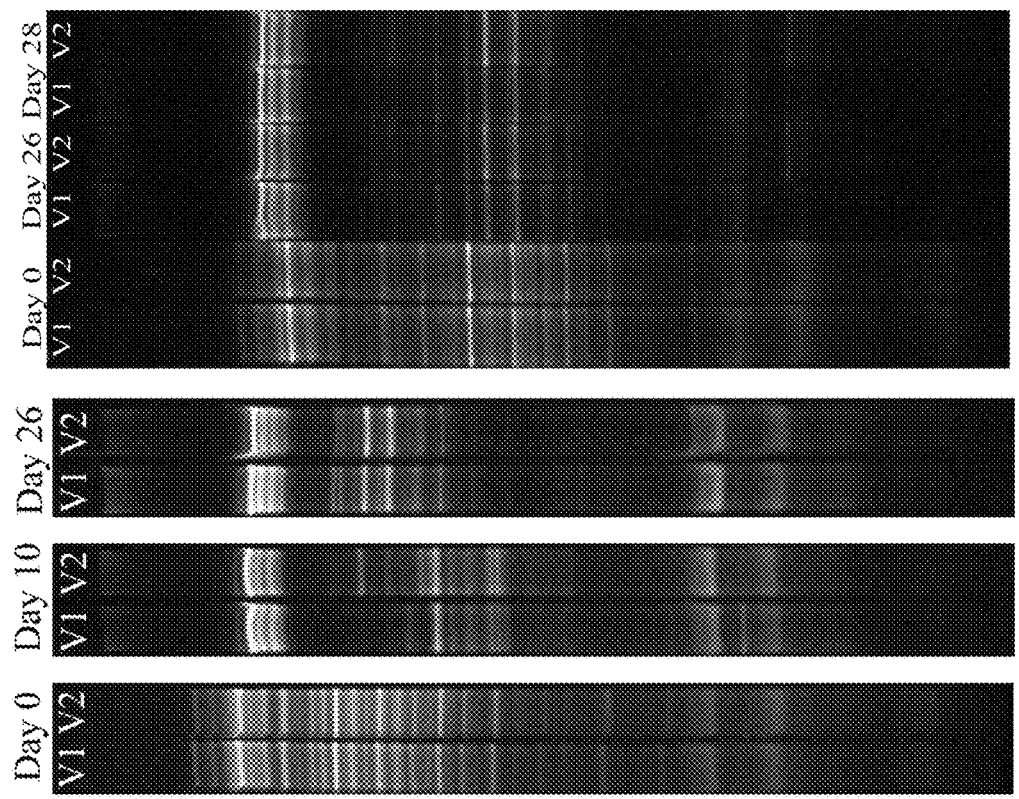
FIGS. 5A-F show the reproducibility of two chemostat vessels (V1 and V2) seeded with identical fecal inoculum from Donor 2. A) DGGE profiles showing communities on days 0, 10, 26 and 28; B) Correlation coefficients (expressed as percentages) comparing the profiles of each vessel at the same time point, plotted over the course of the experiment; C) Community dynamics as shown using moving window correlation analysis. Similarity of the community within each vessel was calculated by comparing the profile of day (x) and day (x−2); D) Shannon Diversity Index (H') plot representing the community diversity of each vessel over the course of the experiment; E) Range weighted richness (Rr) plot representing the richness in each vessel over the course of the experiment; F) Shannon equitability index (EH) plot representing the community evenness values from each vessel over the course of the experiment. Without mucin, two vessels could be run in parallel and maintain identical communities, reaching steady state at about 26-28 days post-inoculation.
Figure 5B:
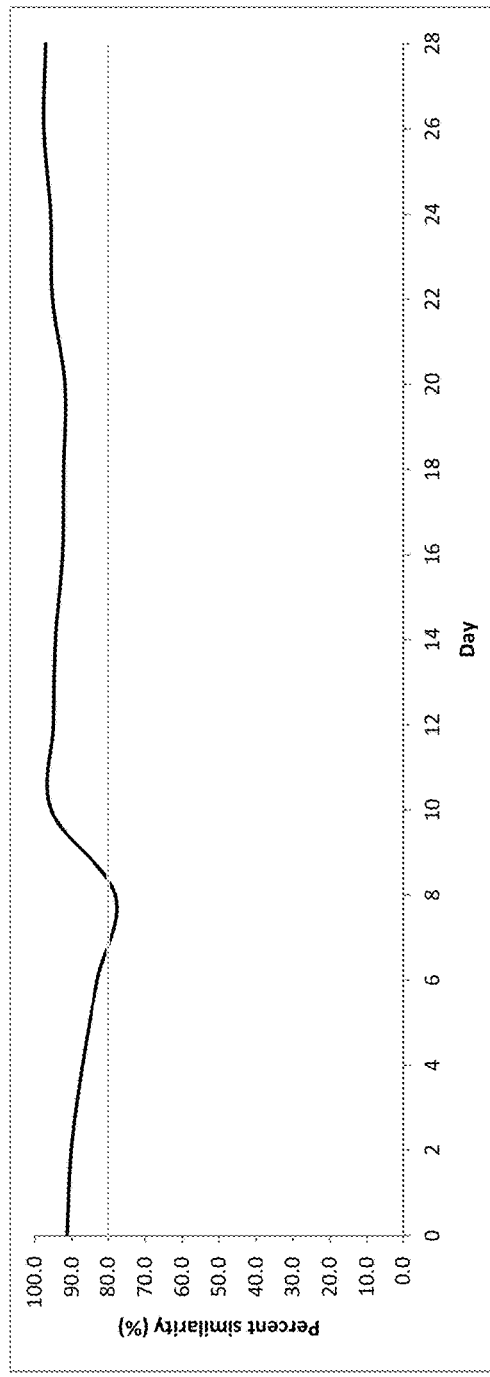
Figure 5C:
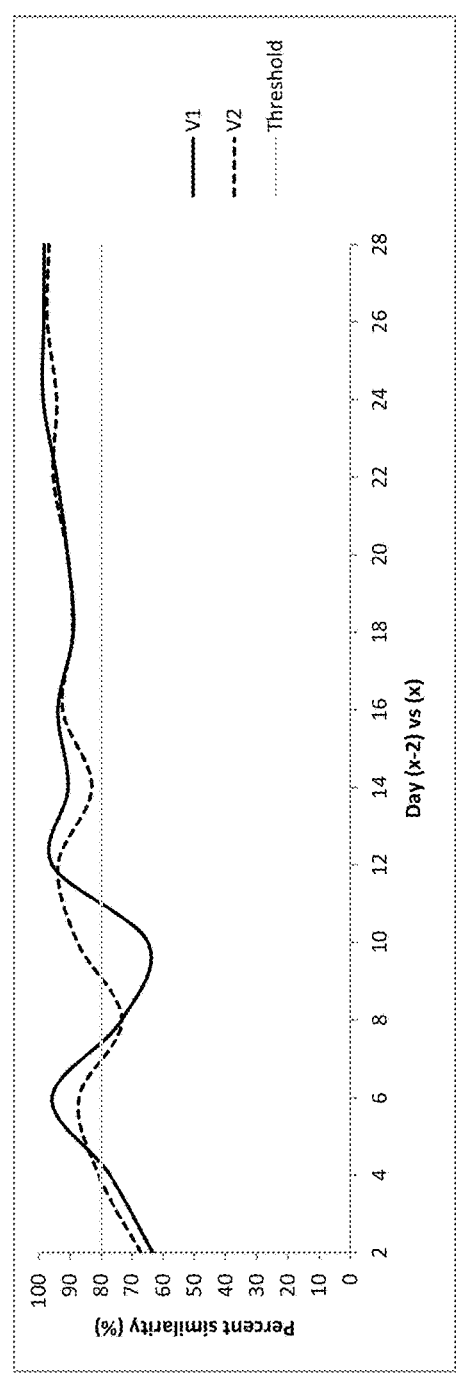
Figure 5D:
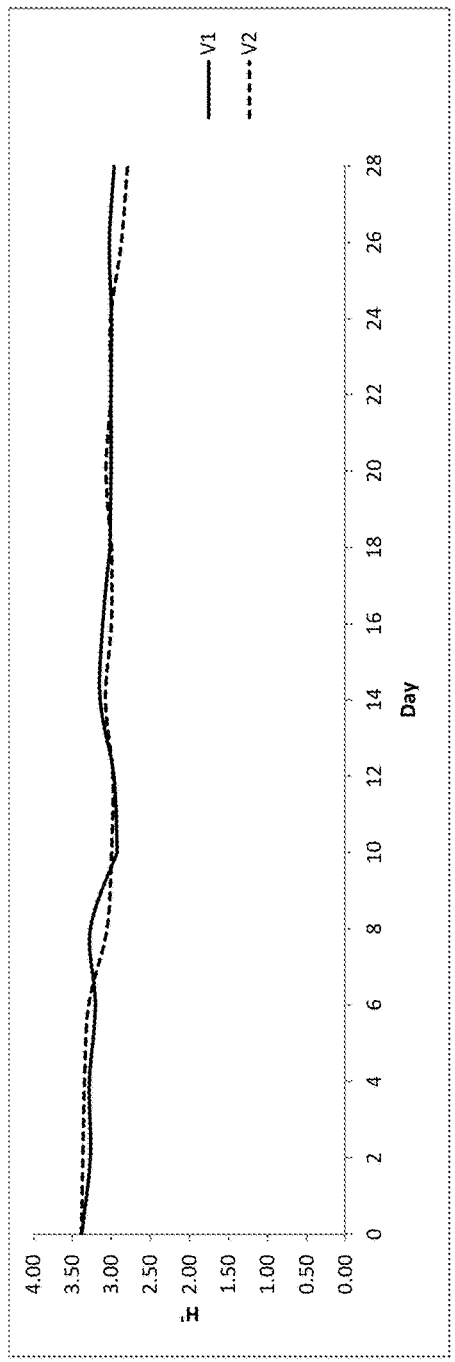
Figure 5E:
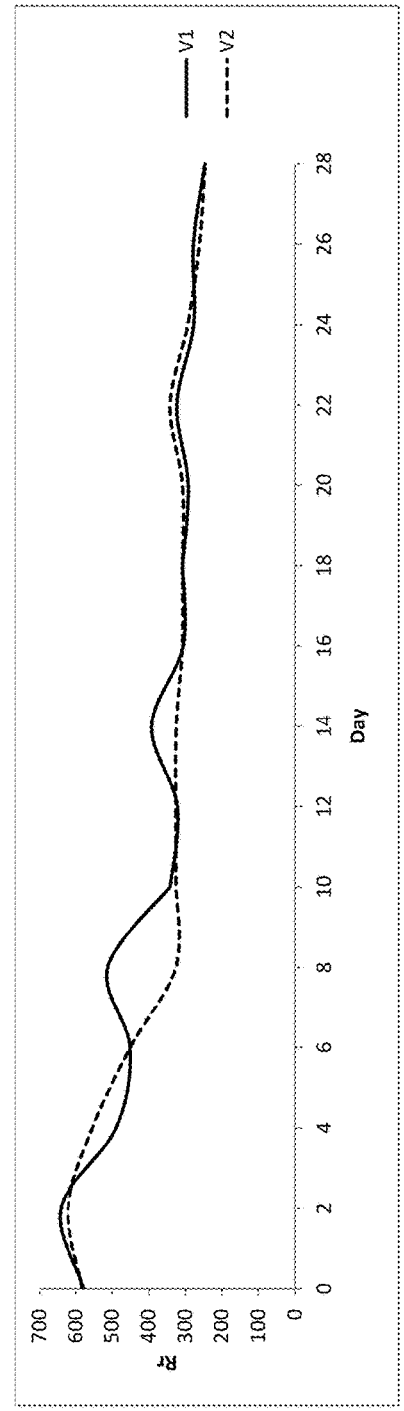
Figure 5F:
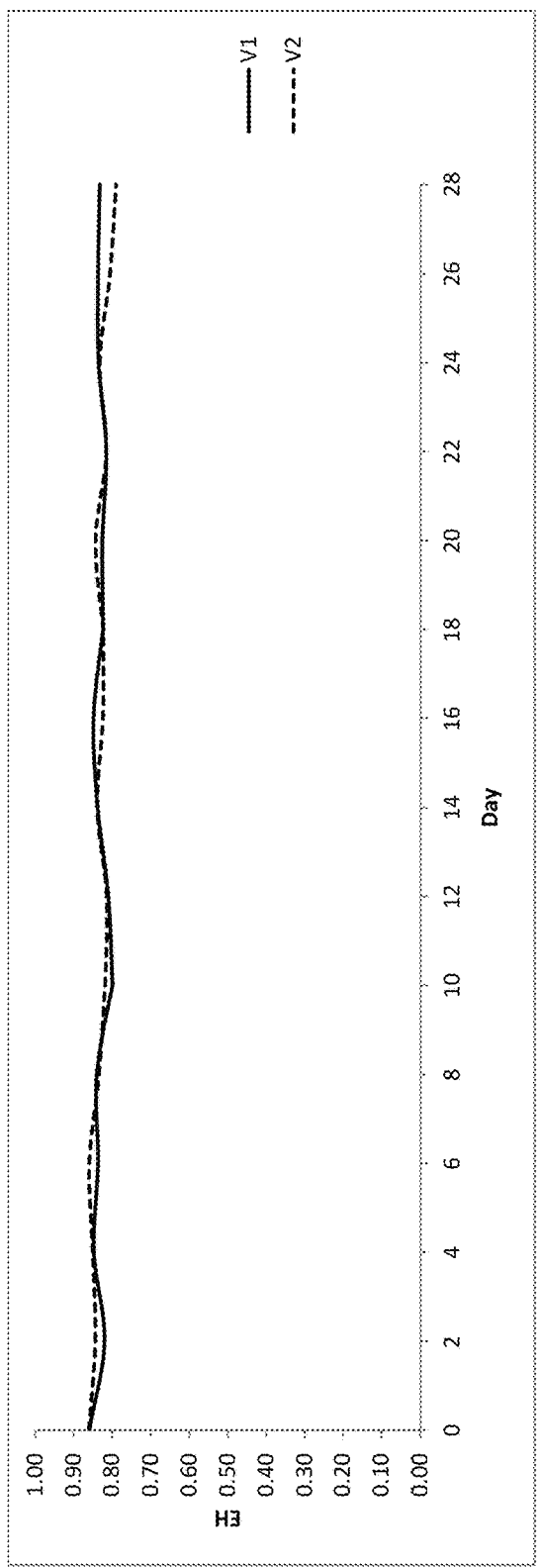
Figure 6A:
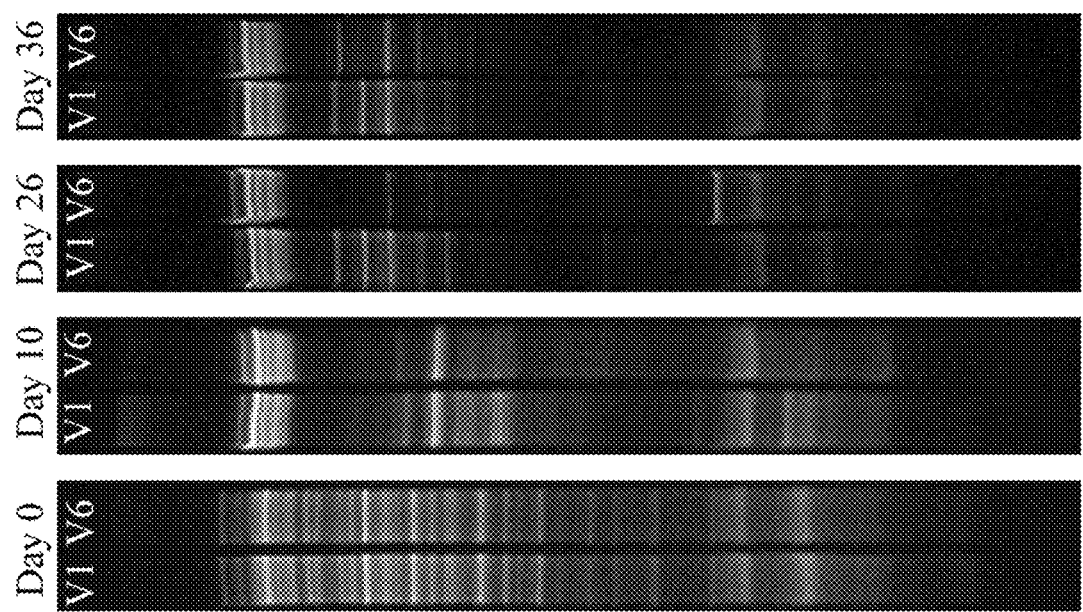
FIGS. 6A-F show a comparison of the chemostat media used in our laboratory ("Medial"; used to feed V1) to a previously published medium (V6; Walker et al., Appl. Environ. Microbiol., 71 (7):3692-700, 2005). The same fecal inoculum (from Donor 2, 10%) was used to seed each vessel. A) DGGE profiles showing communities on days 0, 10, 26 and 36; B) Correlation coefficients (expressed as percentages) comparing the profiles of each vessel at the same time point, plotted over the course of the experiment; C) Community dynamics as shown using moving window correlation analysis. Similarity of the community within each vessel was calculated by comparing the profile of day (x) and day (x−2); D) Shannon Diversity Index (H') plot representing the community diversity of each vessel over the course of the experiment; E) Range weighted richness (Rr) plot representing the richness in each vessel over the course of the experiment; F) Shannon equitability index (EH) plot representing the community evenness values from each vessel over the course of the experiment. Comparison shows that the media recipe we developed (Medial) provides a suitable medium to grow a stable and diverse chemostat community when compared to the previously published medium.
Figure 6B:
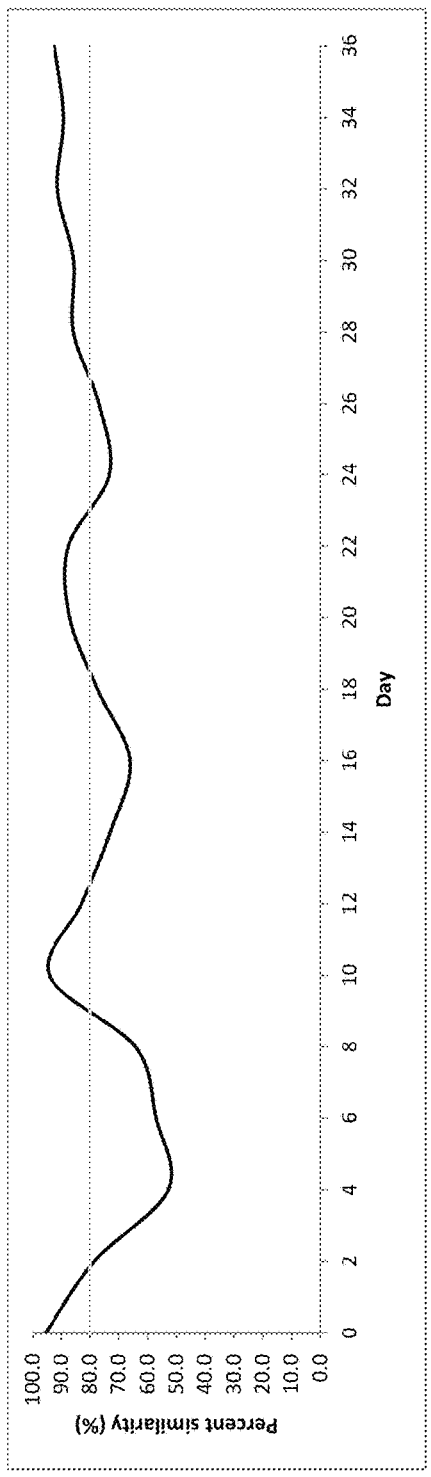
Figure 6C:
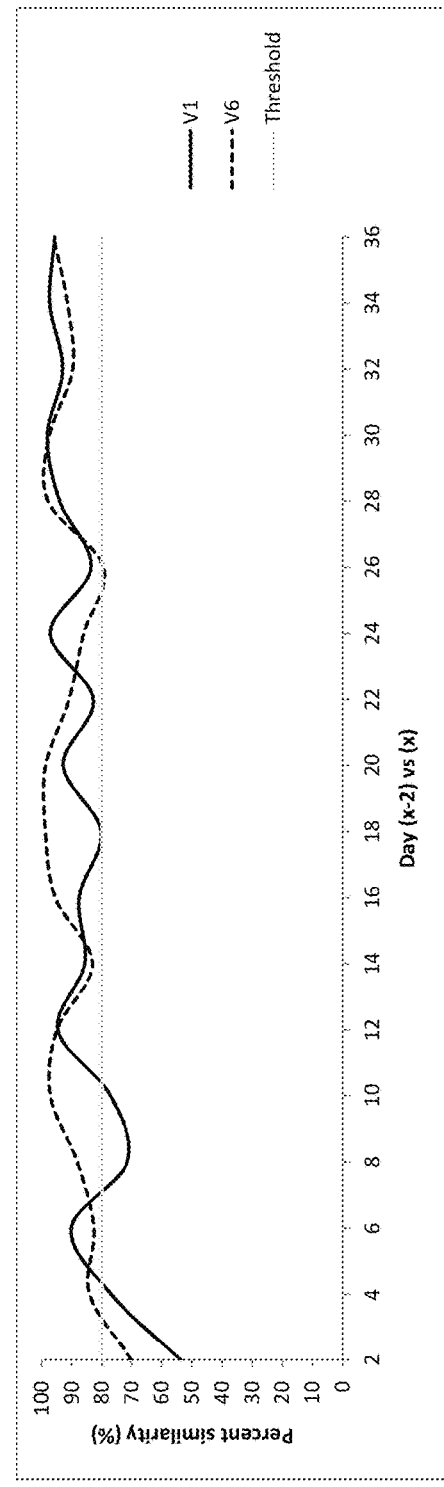
Figure 6D:
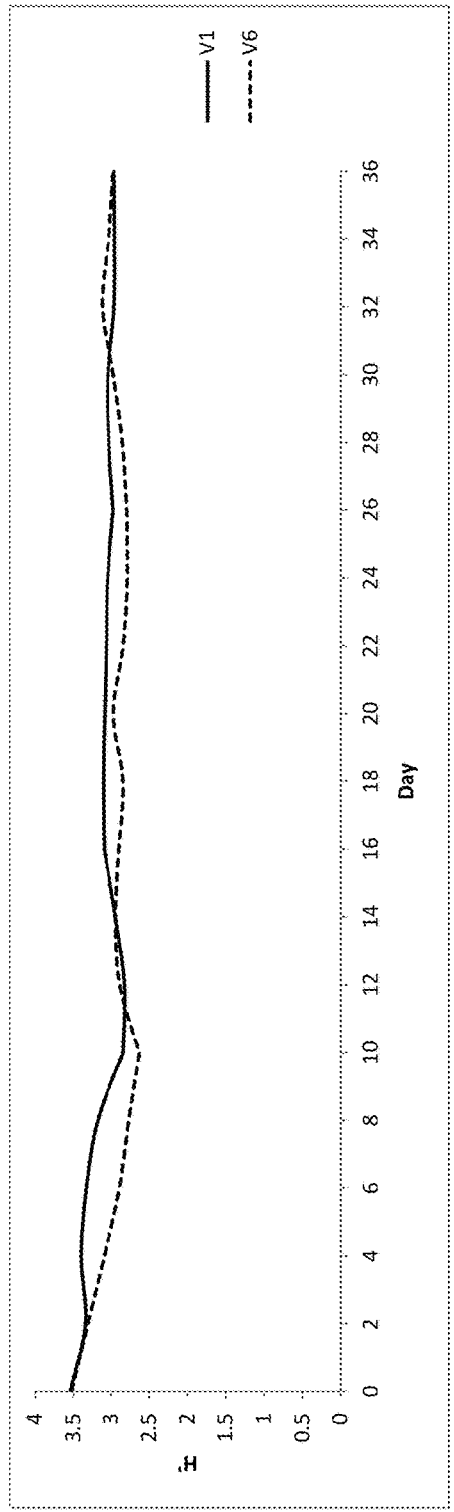
Figure 6E:
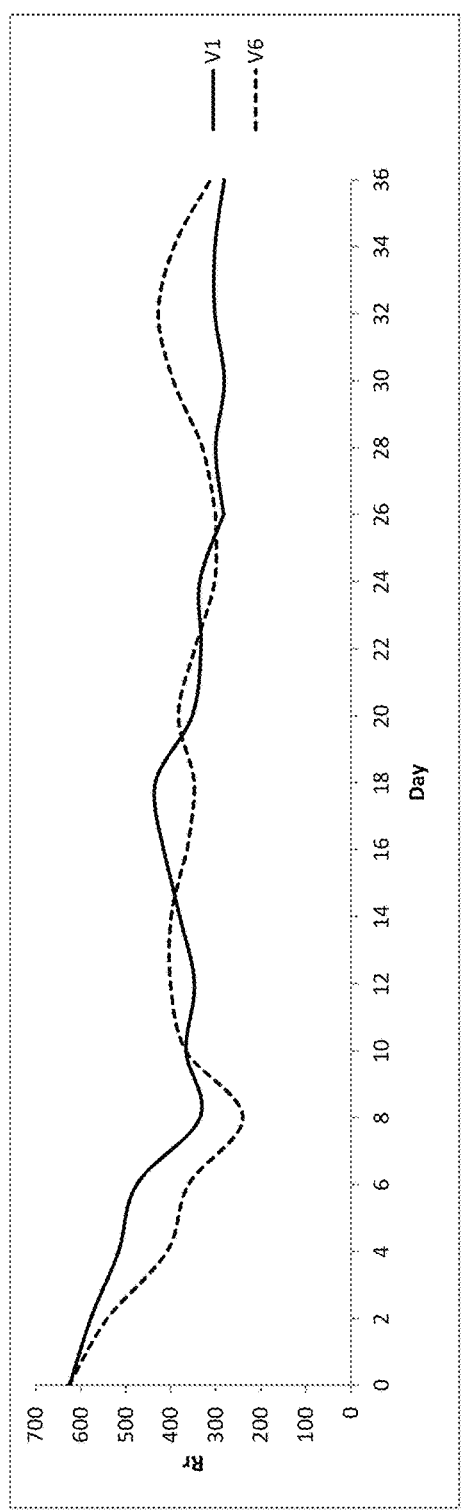
Figure 6F:
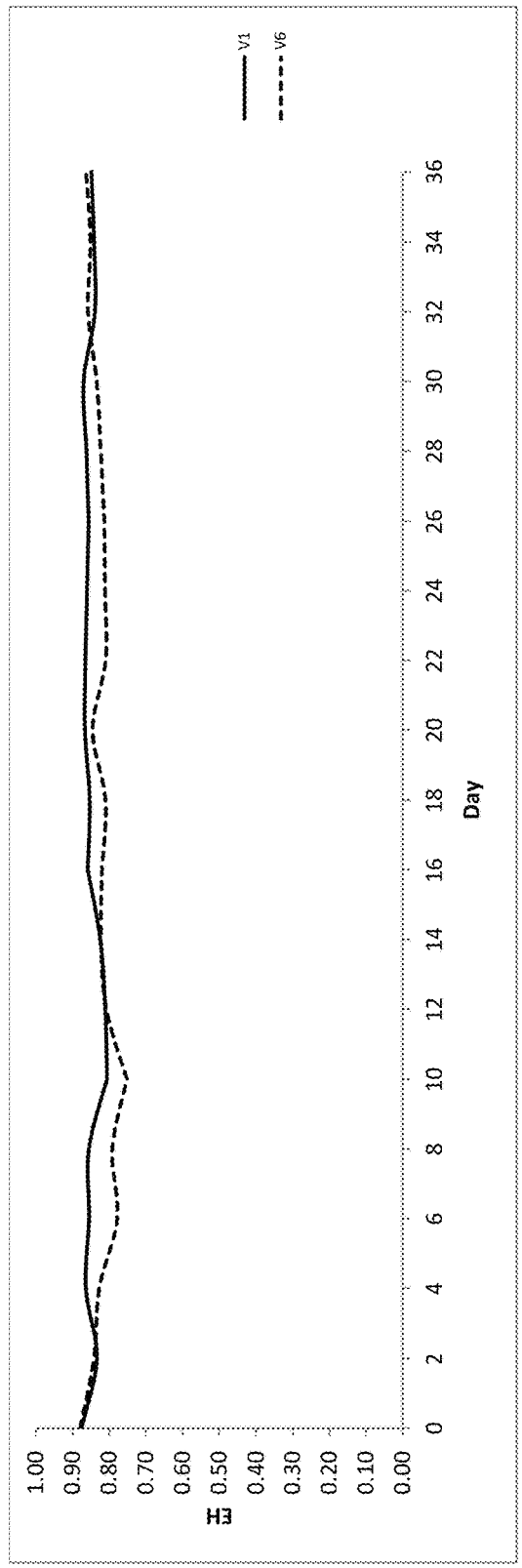
Figure 7B:
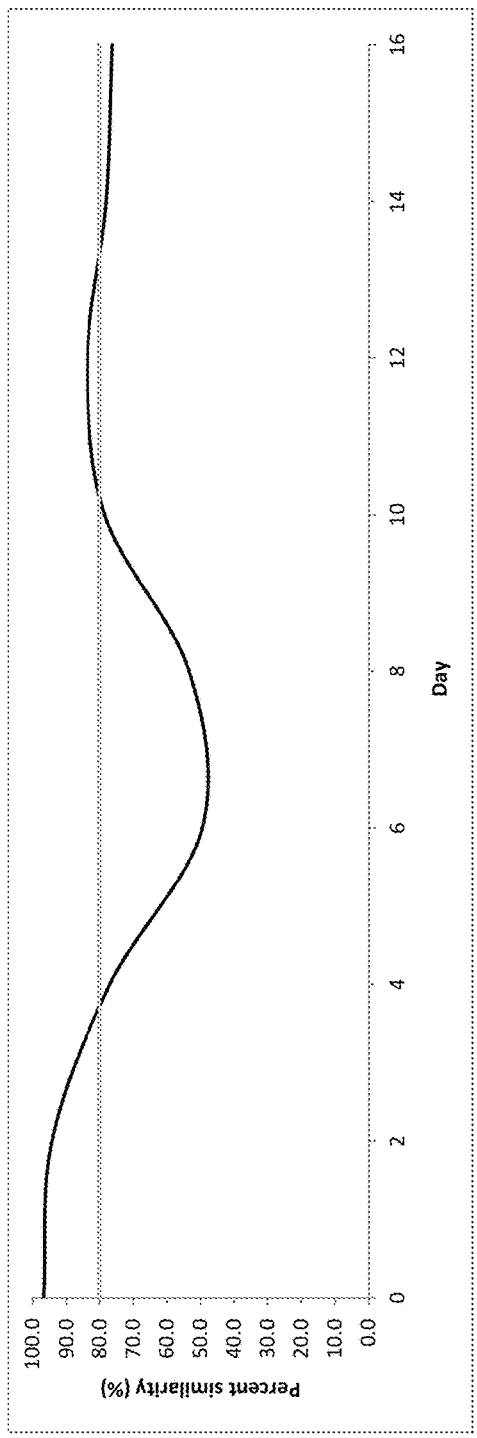
Figure 7C:
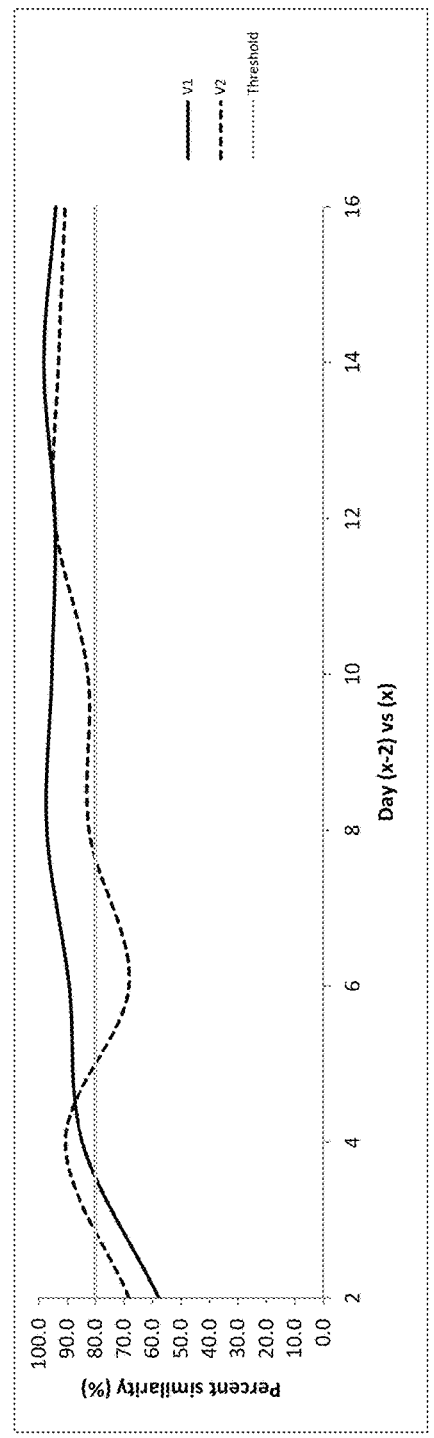
Figure 7D:
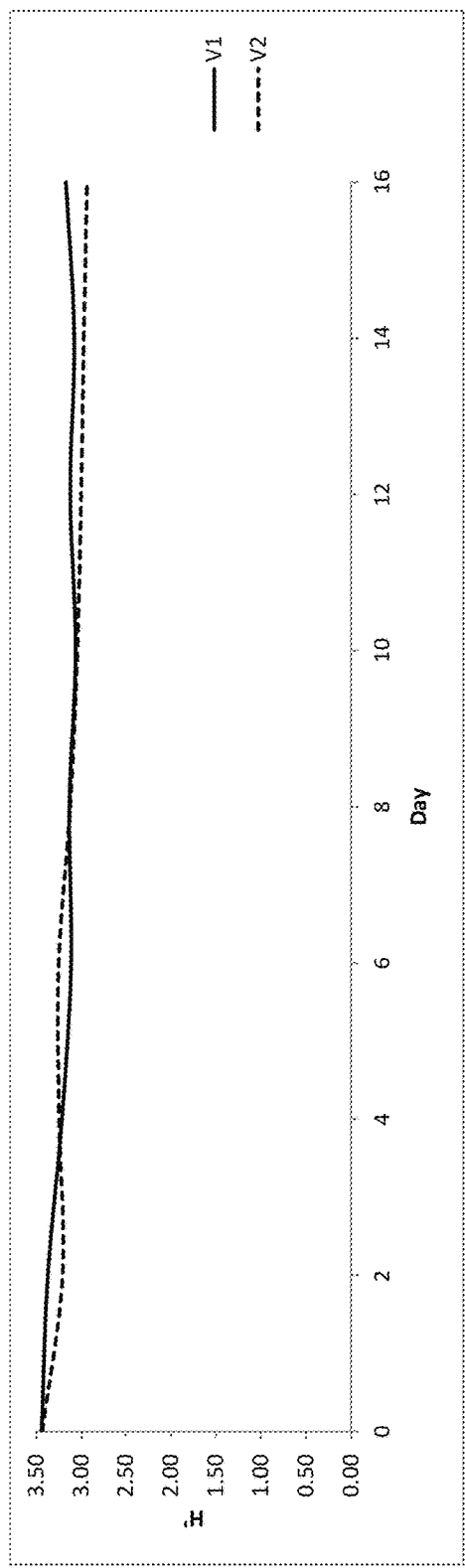
Figure 7E:
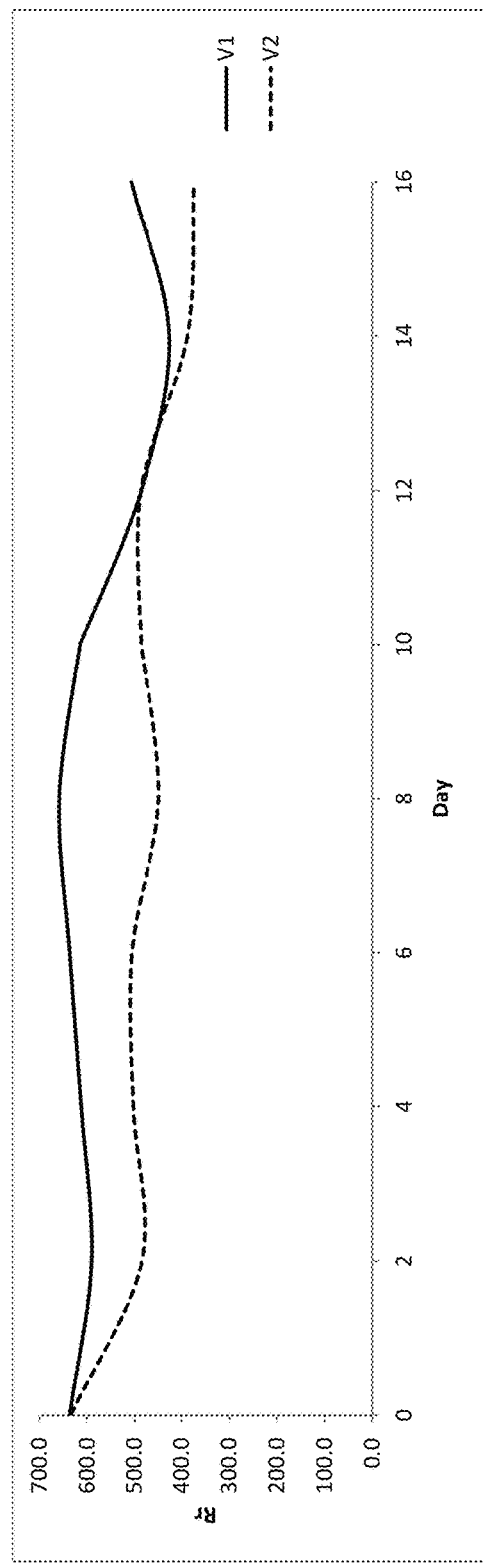
Figure 7F:
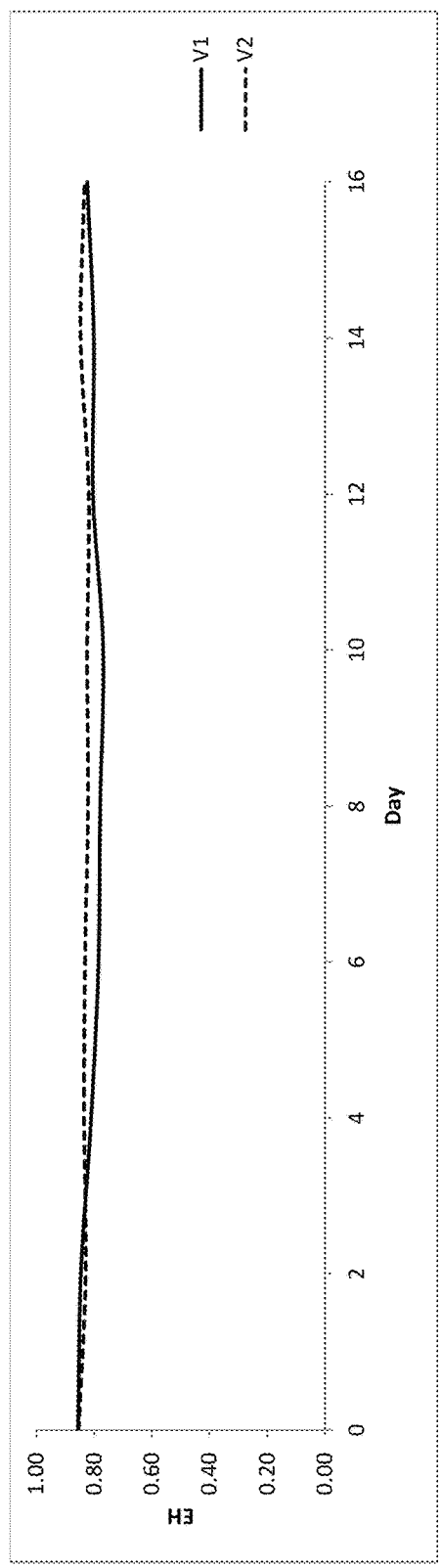
Figure 8A:
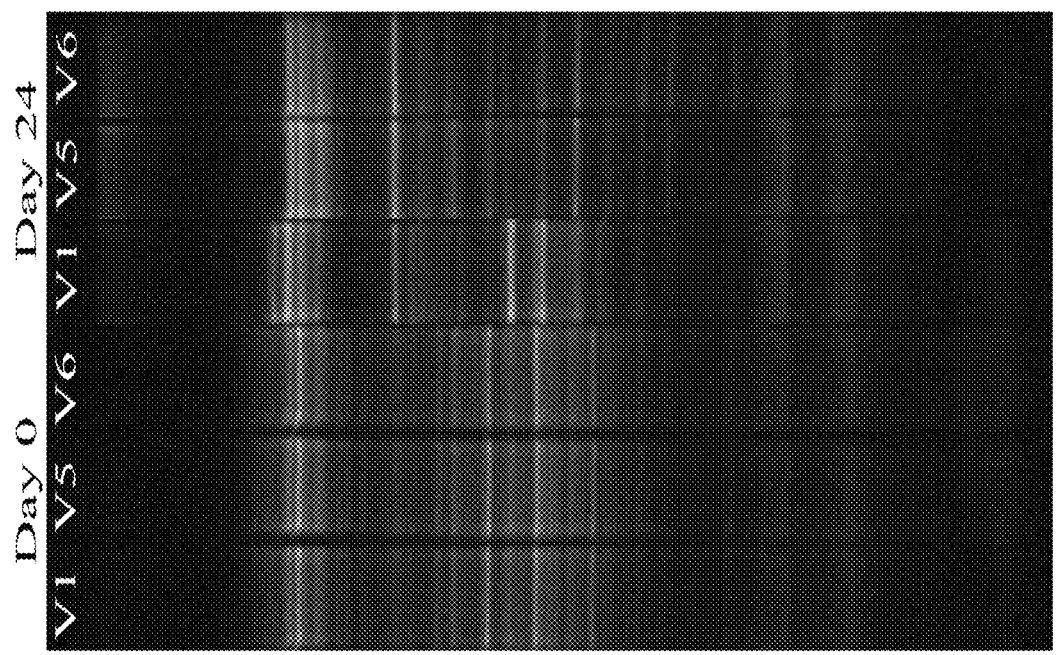
FIGS. 8A-F show the effect of mucin on the diversity of distal gut communities grown in a single-stage chemostat. The same fecal inoculum (from Donor 2, 10%) was used to seed each vessel. A) DGGE profiles showing communities on days 0 and 24; B) Correlation coefficients (expressed as percentages) comparing the profiles of V1 (no mucin) to V5 and V6 (with mucin) on days 0 and 24; C) Correlation coefficients (expressed as percentages) comparing the profiles of V1 (no mucin) to the average values from V5 and V6 (with mucin) on days 0 and 24; D) Shannon Diversity Index (H') representing the community diversity of each vessel on days 0 and 24; E) Range weighted richness (Rr) representing the richness in each vessel on days 0 and 24; F) Shannon equitability index (J) representing the community evenness values from each vessel on days 0 and 24. Addition of mucin to the chemostat resulted in increases in community diversity, richness, and evenness.
Figure 8B:
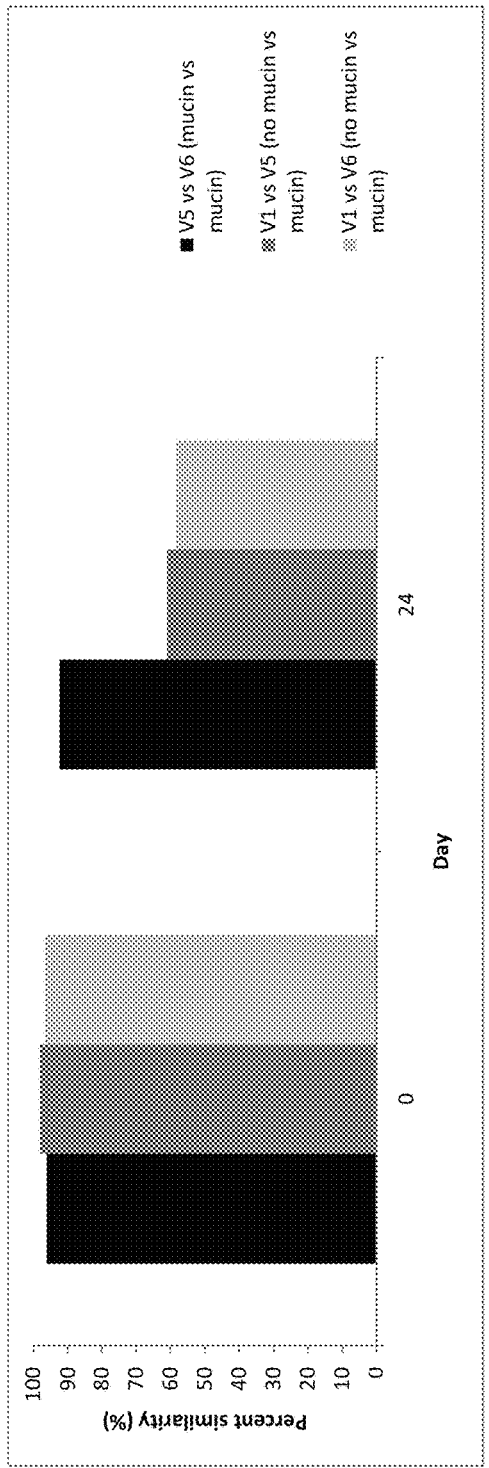
Figure 8C:
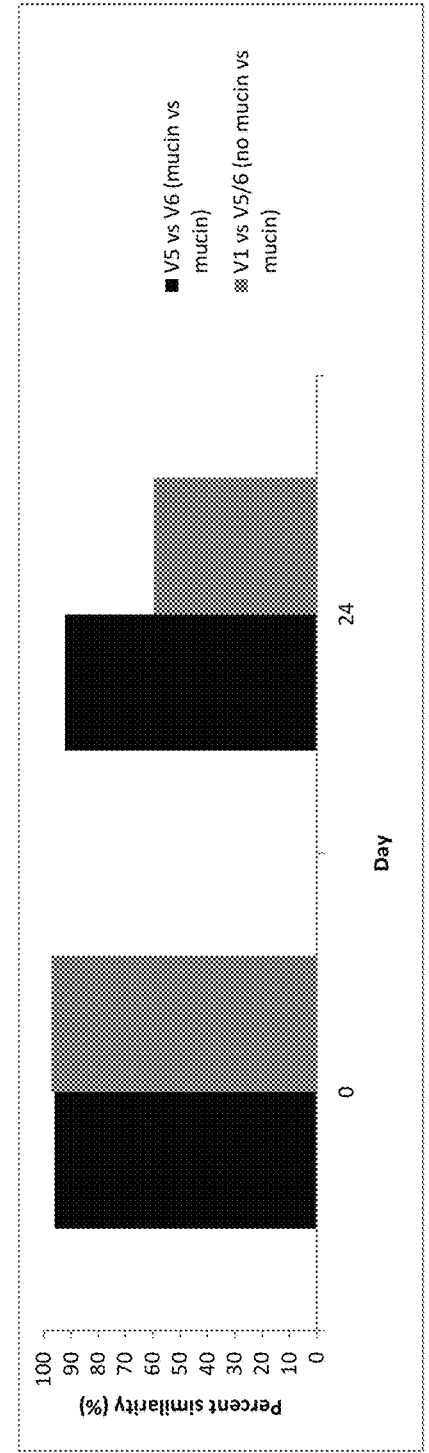
Figure 8D:
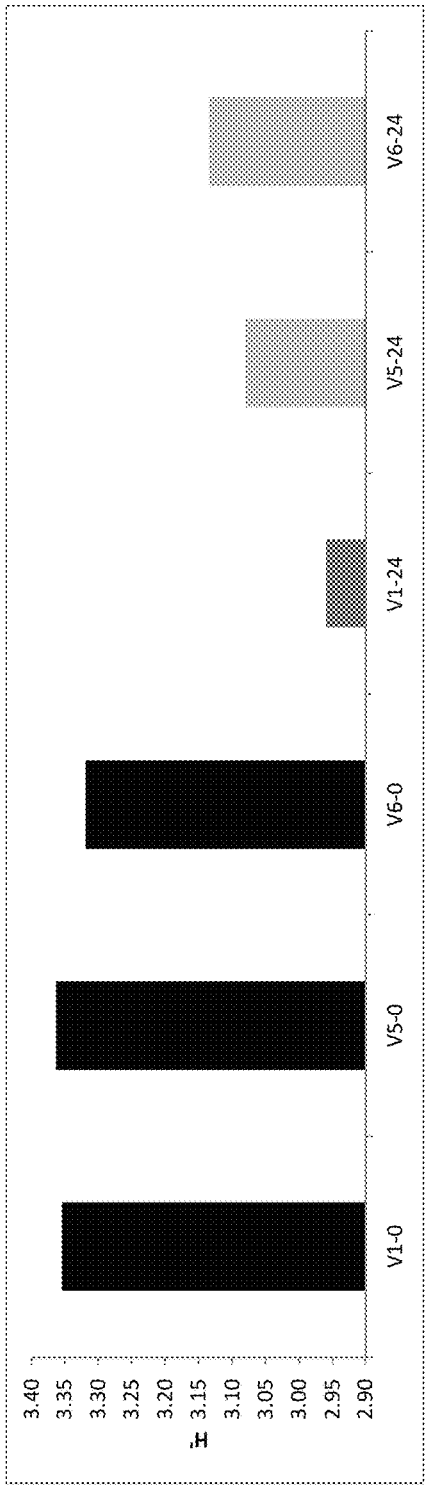
Figure 8E:
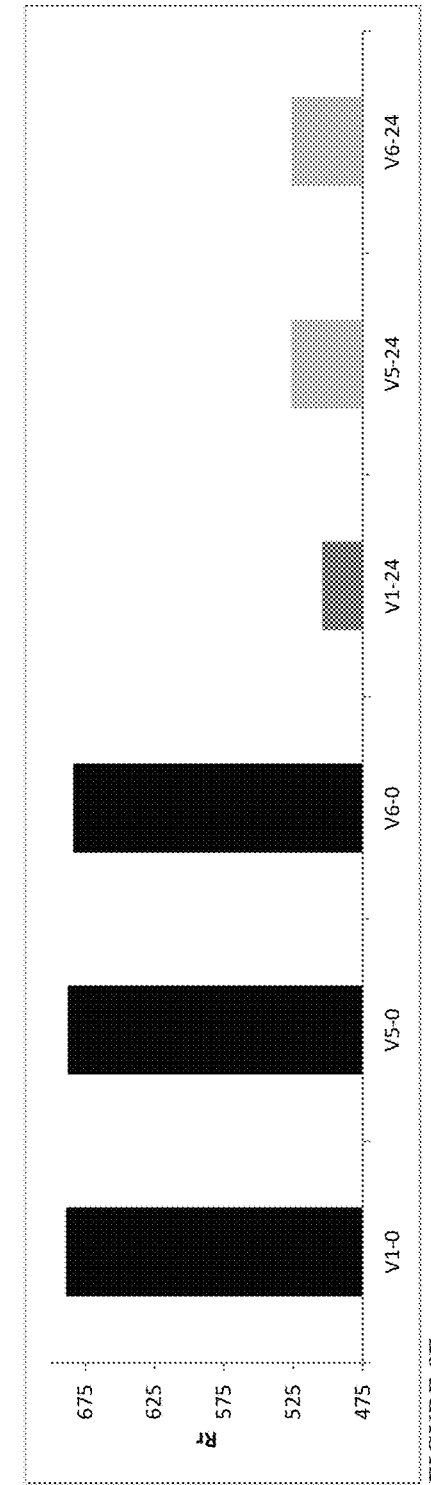
Figure 8F:
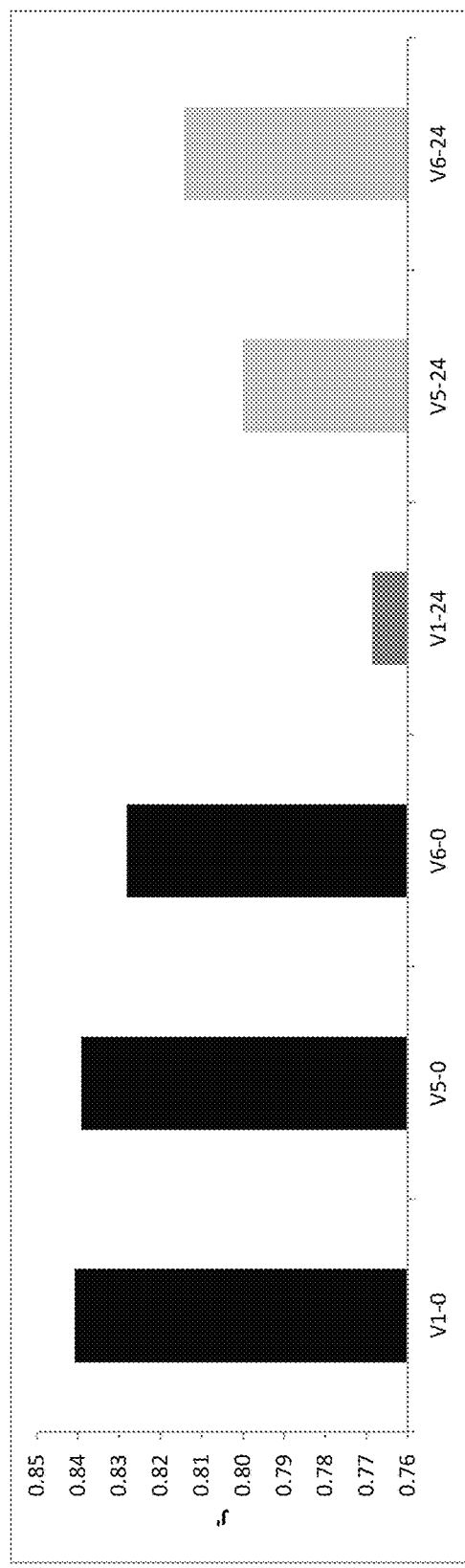
Figure 9:
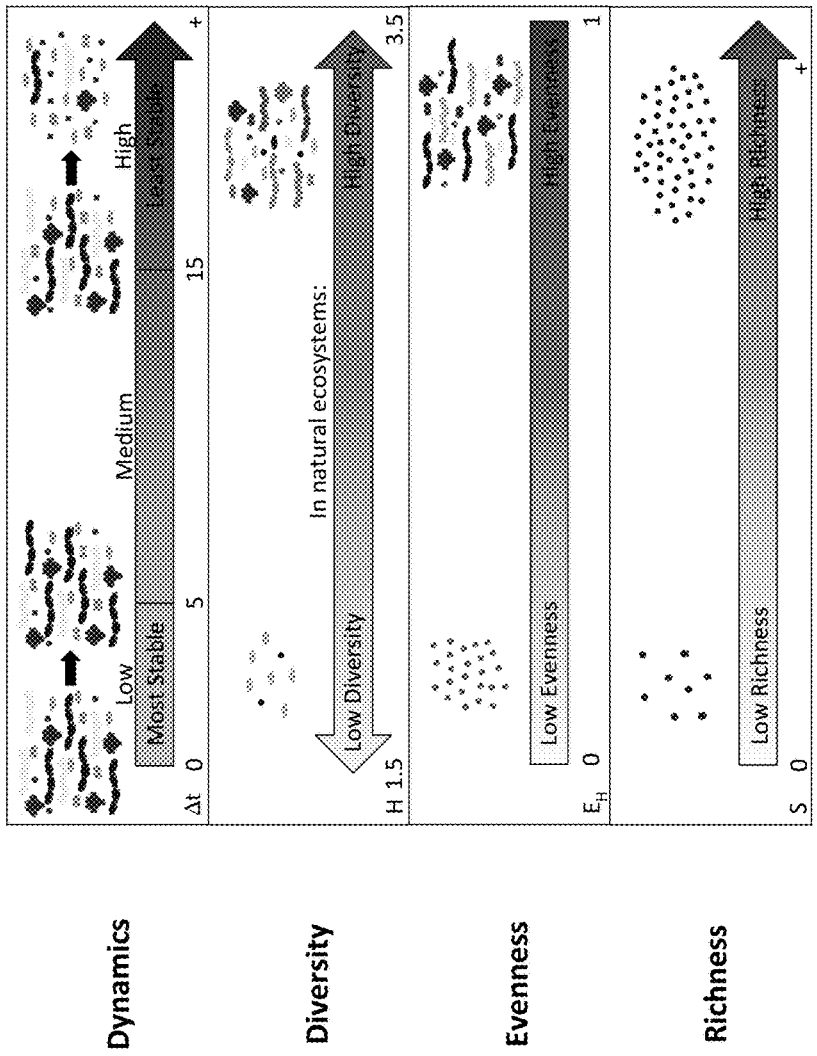
FIG. 9 shows a schematic description of measures used to characterize microbial ecological communities (dynamics, diversity, evenness and richness). The schematic diagram explains basic ecological concepts (including community dynamics, diversity, evenness, and richness). A) Community dynamics represents the changes within the community over a fixed time frame using moving window correlation analysis (Marzorati, M. et al., Environ. Microbiol., 10: 1571-1581, 2008; Possemiers, S. et al., FEMS Microbiol. Ecol., 49: 495-507, 2004); B) Shannon diversity index is a measure of community diversity which takes both species richness (number of species present) and evenness (relative species abundance) into account (Gafan, G. P. et al., J. Clin. Microbiol., 43: 3971-3978, 2005); C) Shannon equitability index describing community evenness, or the degree to which the numbers of individuals are evenly divided between the different species of the community (Pielou, E. C. 1975. Ecological diversity. Wiley, New York); D) Community richness refers to the number of species present in the ecosystem; this measure does not take relative species abundance into account.

DGGE was used to assess whether a 10% or 20% inoculum was better suited to seed a chemostat vessel by maintaining a higher diversity (FIG. 4). Within-group comparisons of the 10% inocula gave a correlation coefficient of 98.1%, while the 20% inocula gave a correlation coefficient of 98.4%. Between-group comparisons of the 10% and 20% inocula gave an average correlation coefficient of 97.9±0.7%. With little differences between the within- and between-group values, little differences in the concentrations of inocula were observed.

There were no differences between the diversity of the 10% and 20% inocula. The Shannon-Weaver index values for both the 10% and 20% inocula were high, with values of 3.38 and 3.37, respectively. Also, the range-weighted richness values for both the 10% and 20% inocula were very high, with values of 802.9 and 810.0, respectively. There were also no differences between the evenness of the 10% and 20% inocula. The 10% and 20% inocula both had Shannon equitability values of 0.82.

Both inocula were similar to the fecal samples, with correlation coefficients of 86.4% for the 10% inocula and 80.9% for the 20% inocula. These inocula were also similar to the respective pellets formed during inocula preparation, with correlation coefficients of 73.7% for the 10% inoculum and 75.5% for the 20% inoculum (Table 5).

TABLE 5

Correlation coefficients for the 10% inocula and the 20% inocula.

| | 10% inoculum | 20% inoculum |
|---|---|---|
| Feces vs. inoculum | 86.4 | 80.9 |
| Inoculum vs. pellet | 73.7 | 75.5 |
| Feces vs. pellet | 86.4 | 85.7 |

Example 5

Comparison of Two Vessels Run in Parallel

DGGE was used to monitor the composition, diversity, and dynamics of two identical chemostat vessels (V1 and V2). Each vessel was seeded with fecal inocula from the same healthy donor to determine whether these two vessels could maintain identical communities.

The inocula used to seed each vessel were very similar to each other and immediately after inoculation the correlation coefficients of samples taken from each vessel was 91.3%. The composition of each vessel varied from each other between days 2-8, however the communities within each vessel became more similar to each other between days 10-28, with an average correlation coefficient of 94.7±2.0%.

GeneTools (statistical analysis software; Syngene) only takes species richness into account when calculating its similarity indices. Both vessels were 95.6% similar to each other on day 10 based on the GeneTools analysis and therefore shared most of their bands between the profiles. However, the vessels differed from each other in terms of the brightness of these bands. Upon visual inspection supported by measures of evenness, both vessels showed identical communities in terms of banding patterns and band brightness by day 26.

During the initial 10 days of the experiment the communities in both vessels were unstable and had high $\Delta t$ values as determined using moving window analysis (FIG. 5). Between days 0-10, both vessels had similar high $\Delta t$ values, with averages of 25.1±13% for V1 and 20.8±9.0% for V2 (p>0.10). Between days 24 and 28, V1 and V2 had similar low dynamics, with $\Delta t$ values of 1.6±0.2% for V1 and 3.9±1.6% for V2 (p>0.10).

The community diversity was very high throughout the duration of the experiment, however an initial drop was observed between days 0 and 10, with Shannon-Weaver index values dropping from 3.38 to 2.93 for V1 and from 3.38 to 3.00 for V2. This drop evened out by day 14, giving an average Shannon-Weaver index value of 3.03±0.06 for V1 and 2.98±0.10 for V2 between days 14 and 28 (p>0.10). The community range-weighted richness also saw a drop between days 0 to 10, with values dropping from 578.6 to 341.7 for V1 and from 582.4 to 325.7 for V2. Like the diversity, the drop in range-weighted richness values evened out by day 14, giving average values of 303.0±43.1 for V1 and 299.0±31.6 for V2 between days 14 and 28 (p>0.10). We also observed a drop in community evenness during the initial 10 days of the experiment. The Shannon equitability values dropped slightly from 0.86 to 0.80 for V1 and 0.86 to 0.82 for V2. This drop evened out by day 14, giving average values of 0.83±0.01 for V1 and 0.82±0.02 for V2 between days 14 and 28 (p>0.10) (Table 6).

To determine the biological significance of our steady-state communities we compared the profiles of our vessels immediately after inoculation to our samples from steady-state (day 26), as shown in FIG. 5. We found that V1 and V2 were 96.3% similar to each other immediately following inoculation, and 96.0% similar to each other 26 days post-inoculation. However, V1 day 0 and V1 day 26 were 40.2% similar to each other, while V2 day 0 and V2 day 26 were 39.3% similar to each other.

TABLE 6

Comparison of two communities cultured separately with fecal inocula from the same healthy donor in Vessel #1 (V1) and Vessel #2 (V2).

| Parameter | V1 | V2 | Time period (Days x-y) | Result of paired t-test |
|---|---|---|---|---|
| Dynamics (Dy) | 25.1 ± 13% | 20.8 ± 9.0% | 0-10 | p > 0.10 |
|  | 1.6 ± 0.2% | 3.9 ± 1.6% | 24-28 | p > 0.10 |

TABLE 6-continued

Comparison of two communities cultured separately with fecal inocula from the same healthy donor in Vessel #1 (V1) and Vessel #2 (V2).

| Parameter | V1 | V2 | Time period (Days x-y) | Result of paired t-test |
|---|---|---|---|---|
| Shannon index (H) | 3.03 ± 0.06 | 2.98 ± 0.10 | 14-28 | p > 0.10 |
| Range-weighted richness (Rr) | 303.0 ± 43.1 | 299.0 ± 31.6 | 14-28 | p > 0.10 |
| Shannon equitability ($E_H$) | 0.83 ± 0.01 | 0.82 ± 0.02 | 14-28 | p > 0.10 |

Example 6

Comparison of Different Media

Our laboratory developed a culture media recipe based on two other recipes found in the literature, as described above (Gibson, G. R., et al., Appl. Environ. Microbiol., 54(11): 2750-5, 1988; Lesmes, U. et al., J. Agric. Food Chem., 56: 5415-5421, 2008). To compare the effectiveness of our culture media (Media 1) we seeded two vessels with the same inoculum from a healthy donor, but used our media to feed one vessel (V1), while using the media recipe by Walker et al., Appl. Environ. Microbiol. 71 (7):3692-700, 2005 to feed the other vessel (V6).

The inocula used to seed each vessel were very similar to each other and immediately after inoculation the correlation coefficients of samples taken from each vessel was 95.5%. Throughout the course of the experiment, the two vessels varied from each other based on their DGGE profiles, with correlation coefficient values fluctuating above and below the 80% similarity threshold between days 2 and 26 (FIG. 6). These vessels were only consistently similar to each other between days 28 and 36, with an average correlation coefficient of 88.9±3.1%.

Between days 28 and 36, both vessels had similar low dynamics as determined using moving window correlation, with $\Delta t$ values of 4.4±2.1% for V1 and 5.5±3.7% for V6 (p>0.10). On day 28, when V1 had already reached steady state, V1 and its inoculum shared a correlation coefficient of 69.4%, while V6 and its inoculum shared a correlation coefficient of 53.9%. On day 36, when V6 reached steady state, V1 and its inoculum shared a correlation coefficient of 67.3%, while V6 and its inoculum shared a correlation coefficient of 60.2%.

The diversity of the communities in both vessels was high throughout the duration of the experiment; however an initial drop in diversity was seen between days 0 and 10. The Shannon-Weaver index values dropped from 3.54 to 2.84 for V1 and from 3.52 to 2.63 for V6 during this period. This drop evened out by day 14, giving average values of 3.02±0.06 for V1 and 2.92±0.10 for V6 between days 14 and 36 (p<0.05). The Shannon index values became similar between days 32 and 36, with average values of 2.96±0.01 for V1 and 3.04±0.07 for V6 (p>0.10). Also during the initial 10 days of this run, the range-weighted richness values dropped in both vessels. These values dropped from 625.2 to 365.5 for V1 and from 626.9 to 366.0 for V6. This drop evened out by day 14, giving average range-weighted richness values of 333.0±52.7 for V1 and 357.8±41.7 for V6 between days 14 and 36 (p>0.10). A drop in community evenness was also observed between days 0 and 10 of the experiment. The Shannon equitability values dropped from 0.88 to 0.81 for V1 and 0.88 to 0.75 for V6. This drop evened out by day 14, giving average values of 0.85±0.01 for V1 and 0.83±0.02 for V6 between days 14 and 36 (p<0.05) (Table 7).

TABLE 7

Comparison of communities in two vessels using different media, Vessel #1 (V1; our media) and Vessel #6 (V6; Walker et al., Appl. Environ. Microbiol. 71 (7):3692-700, 2005 media).

| Parameter | V1 | V6 | Time period (Days x-y) | Result of paired t-test |
| --- | --- | --- | --- | --- |
| Dynamics (Dy) | 4.4 ± 2.1% | 5.5 ± 3.7% | 28-36 | p > 0.10 |
| Shannon index (H) | 3.02 ± 0.06 | 2.92 ± 0.10 | 14-36 | p < 0.05 |
| Range-weighted richness (Rr) | 333.0 ± 52.7 | 357.8 ± 41.7 | 14-36 | p > 0.10 |
| Shannon equitability ($E_H$) | 0.85 ± 0.01 | 0.83 ± 0.02 | 14-36 | p < 0.05 |

Example 7

Comparison of Two Different Retention Times

Two vessels modeling the distal gut were run in parallel in an identical manner, except that the retention time for V1 was set to 65 hours, while the retention time for V2 was set to 24 hours. In this experiment we tested whether an increased retention time would allow the more slow growing bacteria to establish themselves within the vessel and therefore the community, increasing community diversity.

The inocula used to seed each vessel were very similar to each other and immediately after inoculation the correlation coefficients of samples taken from each vessel was 96.7%. While V1 and V2 were reaching steady state they varied from each other and by day 14 the correlation coefficient between V1 and V2 dropped to 78.0%.

FIG. 7 shows each vessel compared to their respective inocula during days 0-10. Over the 10 day period shown V2 was more similar to its inoculum than V1. V1 had an average correlation coefficient of 48.3±2.9% between days 4 and 10 while V2 had an average correlation coefficient of 67.9±5.4% (p<0.01). Comparisons between the inocula and samples taken on day 10 showed that V2 maintained a community that was more similar to its inoculum, with a correlation coefficient of 75.7% for V2 and only 50.5% for V1.

Differences in community dynamics were observed during the first 16 days of the experiment using the two different retention times. Between days 10-16, V1 had a Δt value of 4.4±1.9% while V2 had a Δt of 9.9±6.5% (p>0.10). If the experiment had been allowed to run longer, we would have expected to see a decrease in the dynamics of the community to a value more similar to that of V1, as discussed previously.

An initial drop in community diversity was noted between days 0 and 10 of the experiment. During this period the Shannon-Weaver index values dropped from 3.44 to 3.06 for V1 and from 3.44 to 3.05 for V2. These drops evened out by day 10 giving average values of 3.11±0.05 for V1 and 2.99±0.05 for V2, between days 10 and 16 (p>0.05). There was also an initial drop in range-weighted richness values for each vessel, with values dropping from 636.5 to 614.5 for V1 and from 633.9 to 486.1 for V2 between days 0 and 10. By day 10 V1 and V2 began to have similar average range-weighted richness values, with 508.3±78.5 for V1 and 433.6±61.2 for V2 between days 10 and 16 (p>0.10). Following the pattern observed in the other experiments, a drop in evenness was observed between days 0 and 10. The Shannon equitability values dropped from 0.86 to 0.77 for V1 and 0.85 to 0.79 for V2. This drop evened out by day 10, giving average values of 0.80±0.02 for V1 and 0.83±0.01 for V2 between days 10 and 16 (p>0.05) (Table 8).

TABLE 8

Comparison of communities in two vessels run with different retention times, Vessel #1 (V1; retention time of 65 hours) and Vessel #2 (V2; retention time of 24 hours).

| Parameter | V1 | V2 | Time period (Days x-y) | Result of paired t-test |
| --- | --- | --- | --- | --- |
| Dynamics (Dy) | 4.4 ± 1.9% | 9.7 ± 5.3 | 10-16 | p > 0.10 |
| Shannon index (H) | 3.11 ± 0.05 | 2.99 ± 0.05 | 10-16 | p > 0.05 |
| Range-weighted richness (Rr) | 508.3 ± 78.5 | 433.6 ± 61.2 | 10-16 | p > 0.10 |
| Shannon equitability ($E_H$) | 0.80 ± 0.02 | 0.83 ± 0.01 | 10-16 | p > 0.05 |

Example 8

Effect of Mucin on Gut Communities

Mucin is an important carbon source for the microbial communities of the distal colon (Derrien, M. et al., Gut Microbes, 1 (4):254-268, 2010). To determine whether mucin addition to our culture media would allow us to develop communities which are more diverse and more similar to the starting fecal material, we seeded three vessels with the same inoculum from a healthy donor. One vessel was fed using our culture media without mucin (V1), while two other vessels were fed using our culture media supplemented with 4 g/L mucin (V5 and V6).

The inocula used to seed each vessel were very similar to each other and immediately after inoculation the similarity of samples taken from each vessel ranged from 96.1% to 98.1% (FIG. 8). On day 24, the communities in V5 and V6 shared a 92.4% similarity, the communities in V1 and V5 shared a 61.0% similarity, and the communities in V1 and V6 shared a 58.4% similarity (FIG. 8).

The communities in each vessel at day 24 were also compared to the communities in each vessel at day 0. For V1, communities at day 0 and day 24 were 56.5% similar; for V5, communities at day 0 and day 24 were 59.6% similar; and for V6, communities at day 0 and day 24 were 48.9% similar.

The diversity in each vessel dropped between days 0 and 24, however there was a larger decrease in diversity in the vessel without mucin (V1) than there was in the vessels with mucin (V5, V6), as shown in FIG. 8. The average Shannon-Weaver index value of all three vessels on day 0 was 3.35±0.02. At 24 days post-inoculation, the Shannon-Weaver index values dropped to 2.96 for V1, 3.08 for V5, and 3.13 for V6.

The richness in each vessel also dropped between days 0 and 24, however there was a slightly larger decrease in richness in the vessel without mucin (V1) than there was in the vessels with mucin (V5, V6), as shown in FIG. 8. The average range-weighted richness value of all three vessels on day 0 was 686.8±2.8. At 24 days post-inoculation, the range-weighted richness values dropped to 504.2 for V1, 526.8 for V5, and 526.2 for V6.

Finally, the evenness in each vessel dropped between days 0 and 24. There was a larger decrease in evenness in the vessel without mucin (V1) than there was in the vessels with mucin (V5, V6), as shown in FIG. 8. The average Shannon equitability index value of all three vessels on day 0 was 0.84±0.01. At 24 days post-inoculation, the Shannon equitability index values dropped to 0.77 for V1, 0.80 for V5, and 0.81 for V6.

In sum, we have developed and characterized microbial communities from the human distal colon that were stable, reproducible, and biologically significant in a single-stage chemostat model of the gut. We fully characterized the diversity, stability, and similarity of these communities and also characterized the fecal inoculations from the starting material to use as a point of reference when analyzing our simulated communities. We show that the microbial communities are physiologically relevant, steady-state communities having reproducible starting points. The in vitro communities closely mimic the communities of the distal gut microbiota. We also compared several fecal inocula from Donor 2 over an 8 month period, and found that the predominant bacterial species from this healthy donor remained stable over time (not shown). These values provide us with a baseline to which we can compare our chemostat community values. Our microbial chemostat communities maintained similar high diversity, richness, and evenness values.

The results also show that one can develop reproducible communities in our chemostat model as this donor fulfills our criteria to donate (healthy, no recent history of antibiotics), as one can collect a stool sample to use in future experiments that will share similar profiles to a stool sample taken at an earlier time. This means that similar steady-state communities can be established that can be compared between chemostat runs using complex microbial communities prepared from fresh fecal samples.

Comparison of the fecal community from four different healthy donors showed that each donor had a unique profile (as expected, Tannock G. W., Eur. J. Clin. Nutr., 56 Suppl 4:S44-9, 2002). However, all four profiles showed similar diversity, richness, and evenness values. This suggests that the fecal microbiota from different healthy individuals share similar levels of diversity (as assessed by DGGE).

We used DGGE to assess whether there was a significant difference between 10% and 20% inocula used to seed a chemostat vessel in terms of community structure and diversity. Based on the % similarity, we found similar within- and between-group differences for both concentrations of inocula. Both communities also had similar community diversity, richness, and evenness values. However, one obvious difference between the two concentrations of inocula is the thickness of the inocula, as the 20% inoculum was much thicker than the 10% inocula. This made inoculation with the 20% inocula much more difficult. This, together with the fact that the 10% and 20% inocula were very similar as assessed by DGGE, meant that a 10% inoculum was used for all future studies.

We also compared the two concentrations of inocula to the starting fecal material to assess whether the protocol used to prepare the inocula might have altered the microbial community structure. We found that both the 10% and 20% inocula were composed of microbial communities which were representative of the starting feces. This result shows that our protocol does not cause the inoculum to vary significantly from the feces it was derived from, making it a relevant seeding material to simulate the in vivo community in our chemostat model. Differences between the fecal inocula (the supernatant) and the pellet formed after centrifugation of the fecal slurry may be due to bacteria adherent to food residues that did not detach when homogenized. As these populations probably represent more specialized niches, they are not representative of the general luminal populations of interest for our studies.

Example 9

Supplementing Microbial Growth Using Liquid Gold

Liquid Gold was obtained by filter-sterilization of a donor-seeded chemostat sample, as described above. In brief, the sample was centrifuged at 14,000 rpm for 10 minutes and the supernatant was filtered sequentially through different sized syringe filters in the following order: 1.0 μm, 0.8 μm, 0.45 μm and finally 0.22 μm. Sequential filtration was required to allow removal of sediments, which readily clog the filters. Liquid Gold was used to supplement FAA plates to a final concentration of 3%. Concentrations of 1%, 3%, 5% and 10% have been tested, and 3% was found to be optimal (not shown).

Growth using Liquid Gold-supplemented FAA plates was observed for *Faecalibacterium prausnitzii* and *Ruminococcus callidus* (ATCC27760). For both of these species, no growth was observed using unsupplemented FAA plates. Liquid Gold-supplemented FAA plates yielded ~30 colonies for *Ruminococcus callidus* and ~50 colonies for *F. prausnitzii* when streaked from frozen stocks.

The *F. prausnitzii* strain used here was isolated from Donor 5. Liquid Gold plates supplemented with Donor 5 Liquid Gold was used to grow the strain from frozen stock. *R. callidus* was grown on Donor 5 Liquid Gold supplemented plates and Donor 6 Liquid Gold supplemented plates. Growth was observed for both media types, but plates supplemented with Donor 5 Liquid Gold yielded more growth (30 colonies versus 5), suggesting that there are growth-enhancement relevant differences between Liquid Gold from different sources or donors.

Figures 14A, 14B:
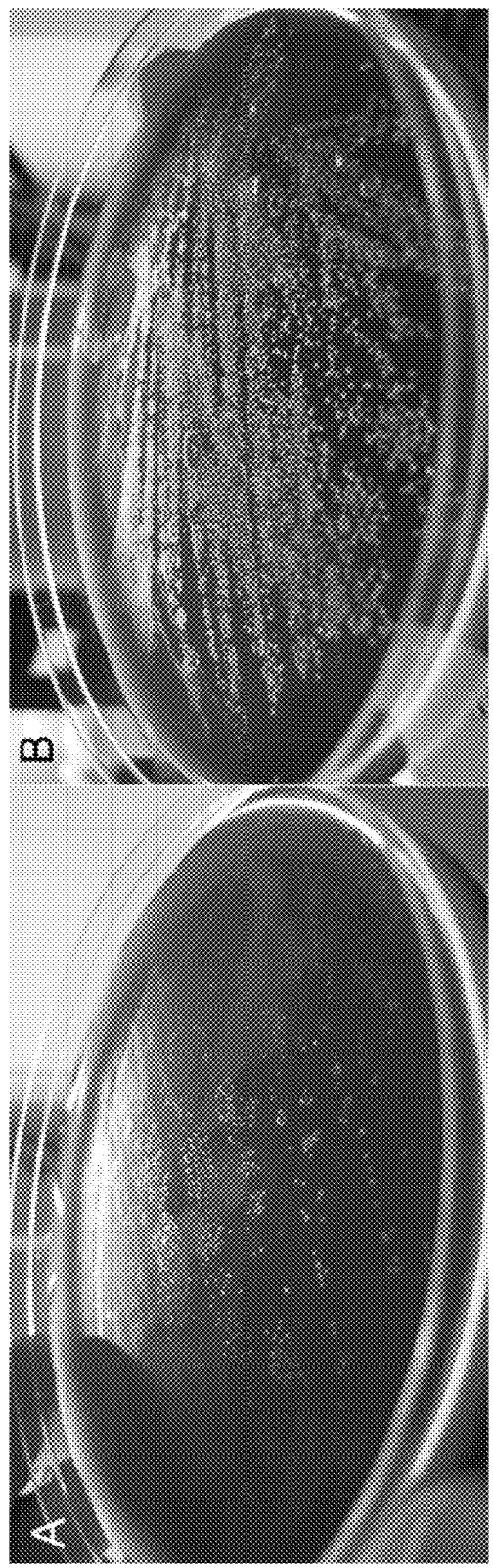
FIGS. 14A-B show representative plates demonstrating growth of the *Faecalibacterium prausnitzii* strain, which showed differential growth in response to Liquid Gold media supplement included in the agar media preparation at 3%. Plates were inoculated with identical inocula and incubated at 37° C. for 3 days under total anaerobic conditions. Plate A: Fastidious anaerobe agar (FAA) supplemented with 5% defibrinated sheep blood alone. Plate B: FAA supplemented with 5% defibrinated sheep blood and 3% filtered (cell-free) Liquid Gold media supplement (from Donor 6). Growth was clearly enhanced by addition of Liquid Gold media supplement to the media.

FIG. 14 shows that growth of the *F. prausnitzii* strain isolated from Donor 5 was enhanced by supplementation of culture media with Liquid Gold media supplement from Donor 6. Plates were inoculated with identical inocula and incubated at 37° C. for 3 days under total anaerobic conditions. Plate A: Fastidious anaerobe agar supplemented with 5% defibrinated sheep blood alone; Plate B: Fastidious anaerobe agar supplemented with 5% defibrinated sheep blood and 3% filtered (cell-free) Liquid Gold (from donor 6). FIG. 14 shows that growth was clearly enhanced by the addition of Liquid Gold to the media at a concentration of 3%.

We have regularly stored Liquid Gold for several months at 4° C., without a noticeable diminishment of effectiveness, indicating that the growth-enhancing qualities of Liquid Gold are stable.

In summary, the above examples show that the methods described herein provide for preparation of stable and reproducible communities, which can be used, e.g., to assess the effect of a treatment on community composition and structure. For example, a "test" vessel can be operated in parallel with a "control" vessel. Running two identical vessels in parallel and ensuring they have identical, steady-state communities at the time of treatment allows one to determine that shifts in the community are due to the treatment, and not to naturally occurring shifts in the community.

As described above, we monitored the colonization of two identical vessels set to mimic the distal colon for 28 days post-inoculation. DGGE was used to monitor the composition, diversity, and dynamics of two identical chemostat vessels (V1 and V2) seeded with identical fecal inocula from a healthy donor. We determined that two vessels could be run in parallel and maintain identical communities.

We used moving window correlation to create stability profiles by plotting the % similarity values between day x and day x−2 (FIGS. 5, 7). There was an increase in the rate of change values as the communities transitioned from an in vivo to an in vitro environment (days 0-10). During this period there was an initial drop in community diversity in both vessels. When we looked more closely at the communities by analyzing the richness and evenness separately, we saw that the drop in diversity was more influenced by the drop in richness than the drop in evenness. After the transition period the communities stabilized and the Shannon index, range-weighted richness, and Shannon's equitability values were identical and reflected a stable community able to maintain high diversity, richness, and evenness.

While the two vessels shared a similar community composition by Day 10, they didn't develop identical bacterial communities that were similar both in terms of species composition and abundance until 26 days post-inoculation. Both communities reached steady state as the rate of change values dropped below 5% by day 26 (achieved for both vessels between days 24-28).

Taken together, the results reported herein show that our single-stage chemostat vessels can be seeded with the same fecal community and produce communities that are stable, reproducible, and diverse, reaching steady state after approximately 26 days post-inoculation. Further, our single-stage chemostat was able to develop two identical steady-state communities which were more similar to each other than communities developed in multi-stage chemostat systems (Van den Abbeele, P. et al., Appl. Environ. Microbiol., 76(15): 5237-46, 2010). In our single-stage chemostat model of the distal gut we found that the communities developed in two identical vessels showed a correlation of 97.6% on day 26. At this time the band brightness in these DGGE profiles was almost identical. Overall, the single-stage chemostat model of the distal gut produced more stable, reproducible communities than those grown previously in multi-stage chemostats.

It is known that the composition of the gut microbiota varies depending on the segment of the intestine being sampled (Mai, V. and Morris, J. G. Jr., J. Nutr., 134(2):459-64, 2004; Marteau, P. et al., Appl. Environ. Microbiol., 67(10):4939-42, 2001). Fresh fecal samples should be used to model the bacterial communities of the distal gut lumen since the fecal bacteria are more representative of the distal gut luminal microbiota than of the microbiota from other segments of the intestine (Possemiers, S. et al., FEMS Microbiol. Ecol., 49(3): 495-507, 2004). Modelling the distal gut in a single-stage system more accurately reflects the in vivo environment to provide more biologically significant results.

In addition, microbial diversity and community composition within the gut is influenced by several physical, biochemical, and physiological factors. One must assure that the simulated community is as similar to the in vivo community as possible if the results are to be extrapolated to the host, so it is important to control and mimic these factors as closely as possible when designing in vitro simulators. Computer-operated process controls of chemostat models allow for experimental parameters such as pH, temperature, feed rate, and oxygen levels to be continuously monitored and automatically adjusted if deviations occur.

As described above, to determine the effectiveness of our media recipe we set up two chemostat vessels: one vessel fed with media prepared according to our recipe (V1), and another vessel fed with media prepared according to a previously published recipe (V6, Walker, et al., Appl. Environ. Microbiol., 71 (7):3692-700, 2005). The community in V1 was more similar to its inoculum than the community in V6, meaning that the vessel fed using the Media 1 culture medium supported a community that was more representative of the fecal microbiota than the community supported by the previously published medium. Both vessels shared similar community dynamics throughout the course of the experiment and similar rate of change values between days 28 and 36. Community diversity and evenness was higher in V1 between days 14 and 36, however, both vessels shared similar range-weighted richness values during this period. While both media can support diverse communities mimicking those of the distal gut, our media recipe supports a community that is more similar to the inoculum. Based on these observations, the media recipe we developed provides a suitable medium to grow a stable and diverse chemostat community.

As described above, we also investigated whether an increased retention time would allow the more slow growing bacteria to establish themselves within the vessel during the beginning of the experiment (and therefore establish themselves within the community), increasing community diversity. We did this to ensure that the system retention time currently being used (24 hours) was not high enough to prevent certain slow growing populations from surviving within the system. We set up two chemostat vessels with different retention times (V1 and V2). V1 had a longer retention time (65 hrs), while V2 had a shorter, more biologically relevant retention time (24 hrs). DGGE analysis showed that both vessels developed different communities over time (see Table 8). Of these two communities, V2 with a 24 hr retention time developed a community that was more similar to its inoculum than the community developed in V1. Both vessels had similar community dynamics; however the dynamics in V2 was more variable. Both vessels were similar to each other in terms of community diversity, richness, and evenness. Overall, increasing the retention time from the biologically significant value of 24 hours to 65 hours resulted in a community which was less similar to its inoculum and did not maintain a higher level of diversity.

We also compared the colonization process in three chemostat vessels: one vessel fed with a medium without mucin (V1), and two identical vessels fed with a medium supplemented with mucin (V5 and V6). While no differences were observed between all three vessels on day 0, by day 24 the vessels supplemented with mucin were similar to each other, but different from the vessel that was not supplemented with mucin. The addition of mucin to the chemostat resulted in increases in community diversity, richness, and evenness. The addition of mucin also allowed for the development of communities which were more similar to the inoculum than communities without mucin. These results show that it could be advantageous, in certain embodiments, to include mucin as part of the culture medium recipe.

Analysis of samples using the Shannon diversity index, range-weighted richness, and Shannon equitability across several gels resulted in variability in values for the same samples. To correct for this, we ran the same samples at the end of one gel and the beginning of the next gel. For example, if the first gel contained the samples from days 0-10, the next gel would contain the samples from days 10-20, and the next gel would contain the samples from days 20-30, etc. We then added or subtracted the calculated values for the overlapping days to correct for any variation between gels. While the variability of the Shannon diversity index and Shannon equitability values were relatively small, larger variation was seen in the range-weighted richness values. While between-gel variability is an inherent drawback of using DGGE, it still provides us with estimates of community composition and structure. More detailed analyses (such as metagenomic analyses) can also be performed.

In conclusion, we have demonstrated that our single-stage model of the human distal gut supported complex communities which were stable, reproducible, and diverse. We also presented data to support our optimized operational parameters including inoculum concentration, media recipe, and system retention time.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

We claim:

1. method of isolating anaerobic bacteria from human gut, comprising:
(a) culturing a fecal sample comprising a microbial community of the human gut in culture media in a single-stage chemostat under conditions replicating normal human colonic gastrointestinal tract, until equilibrium is reached;
(b) diluting the culture and plating onto anaerobe agar supplemented with a media supplement, and optionally supplemented with defibrinated sheep blood, wherein the media supplement
comprises a filtrate of effluent from a chemostat vessel in which a target bacterial ecosystem has been cultured, wherein the target bacterial ecosystem has been cultured in media comprising: 0.2% w/v Peptone: 0.2% w/v Yeast extract 0.2% w/v $NaHCO_3$: 0.2% w/v Pectin; 0.2% w/v Arabinogalactan; 0,3% w/v Casein; 0,5% w/v unmodified wheat starch: 0.1% w/v inulin; 0,05% w/v bile salts; 0.05% w/v L cysteine HCl; 0.0001% w/v $CaCl_2$; 0.0001% w/v NaCl; 0.0004% w/v $K_2HPO_4$: 0.0004% w/v $KH_2PO_4$; 0.0001% w/v $MgSO_4$; 0.00005% w/v Hemin; and 0.00001% w/v menadione; and
wherein the target bacterial ecosystem comprises Akkermansia muciniphila, *Bacteroides ovatus, Bifidobacterium longum, Collinsella aerofaciens, Dorea longicatena, Eubacterium eligens, Eubacterium rectale, Eubacterium ventriosum, Faecalibacterium prausnitzii, Flavonifractor plautii*, which is formerly *Clostridium orbiscindens, Roseburia intestinalis*, and *Ruminococcus obeum*;
(c) incubating plates in an anaerobe chamber;
(d) purifying individual anaerobic bacterial colonies grown in step (c) to isolate anaerobic bacteria from the human gut; and
optionally, culturing the purified individual anaerobic bacterial colonies from step (d) in liquid culture in a single-stage chemostat under conditions replicating normal human colonic gastrointestinal tract, optionally wherein the media supplement is used to supplement culture media at about 1% v/v to about 10% v/v.

2. The method of claim 1, wherein the anaerobe chamber contains an atmosphere of $N_2$, $CO_2$ or $H_2$, or a mixture thereof.

3. The method of claim 1, wherein the target bacterial ecosystem comprises a human fecal sample.

4. The method of claim 3, wherein the human fecal sample which is cultured is a 10% w/v fecal slurry supernatant or a 20% w/v fecal slurry supernatant.

5. The method of claim 1, wherein the culture media of step a) further comprises 0.2% w/v Xylan.

6. The method of claim 1, wherein the anaerobic bacteria obtained is Faecalibacterium prausnitzii or Ruminococcus callidus (ATCC27760).

7. The method of claim 1, wherein obtaining at least one of the anaerobic bacteria of Faecalibacterium prausnitzii, Ruminococcus callidus (ATCC27760), or a Roseburia species serves as a positive indicator of effectiveness of the method.

* * * * *